United States Patent
Zens

(10) Patent No.: US 10,241,063 B2
(45) Date of Patent: Mar. 26, 2019

(54) MAGNETIC COUPLING HIGH RESOLUTION NUCLEAR MAGNETIC RESOLUTION PROBE AND METHOD OF USE

(71) Applicant: JEOL LTD., Tokyo (JP)

(72) Inventor: Albert Zens, Peabody, MA (US)

(73) Assignee: JEOL LTD., Tokyo (JP)

( * ) Notice: Subject to any disclaimer, the term of this patent is extended or adjusted under 35 U.S.C. 154(b) by 0 days.

(21) Appl. No.: 15/325,425

(22) PCT Filed: Apr. 8, 2016

(86) PCT No.: PCT/IB2016/000730
§ 371 (c)(1),
(2) Date: Jan. 10, 2017

(87) PCT Pub. No.: WO2016/166609
PCT Pub. Date: Oct. 20, 2016

(65) Prior Publication Data
US 2018/0031499 A1 Feb. 1, 2018

Related U.S. Application Data

(60) Provisional application No. 62/148,137, filed on Apr. 15, 2015.

(51) Int. Cl.
*G01N 24/08* (2006.01)
*G01R 33/36* (2006.01)
(Continued)

(52) U.S. Cl.
CPC ......... *G01N 24/08* (2013.01); *G01R 33/3635* (2013.01); *G01R 33/38* (2013.01);
(Continued)

(58) Field of Classification Search
None
See application file for complete search history.

(56) References Cited

U.S. PATENT DOCUMENTS 3,789,832 A 2/1974 Damadian
4,301,410 A 11/1981 Wind
(Continued)

FOREIGN PATENT DOCUMENTS

JP 2008154933 A 12/2006
WO WO2010/018535 2/2010
(Continued)

OTHER PUBLICATIONS

PCT Rule 43bis.1, International Search Report, PCT/IB2016/000730, dated Sep. 11, 2016, 15 pages.
(Continued)

*Primary Examiner* — Melissa J Koval
*Assistant Examiner* — Nasima Monsur
(74) *Attorney, Agent, or Firm* — SCI-Law Strategies, PC

(57) ABSTRACT

In an embodiment of the invention inductive coupling of an idler coil to a parent coil is used to provide a double resonance circuit without the disadvantages of capacitive coupling to the parent coil. In an embodiment of the invention, an inductive coupling coil can be used to achieve a double-tuned circuit. In an embodiment of the invention, a circuit uses inductive coupling to achieve a double resonance circuit for $^1H$, $^{19}F$, and $^{13}C$ experiments where one of the three nuclei are observed and the other two are decoupled. In an embodiment of the invention a pivot or a shunt can be used to couple and decouple the idler coil and the parent coil.

20 Claims, 22 Drawing Sheets

(51) Int. Cl.
*G01R 33/38* (2006.01)
*G01R 33/46* (2006.01)
*G01R 33/34* (2006.01)

(52) U.S. Cl.
CPC .... *G01R 33/4616* (2013.01); *G01R 33/34092* (2013.01); *G01R 33/3642* (2013.01)

(56) References Cited

U.S. PATENT DOCUMENTS

| | | | |
|---|---|---|---|
| 4,398,149 A | 8/1983 | Zens | |
| 4,517,516 A | 5/1985 | Hill | |
| 4,549,136 A | 10/1985 | Zens | |
| 4,609,872 A | 9/1986 | O'Donnell | |
| 4,654,592 A | 3/1987 | Zens | |
| 4,654,593 A | 3/1987 | Ackerman | |
| 4,751,465 A | 6/1988 | Zens | |
| 4,833,412 A | 5/1989 | Zens | |
| 4,947,120 A | 8/1990 | Frank | |
| H1218 H | 8/1993 | Cory | |
| 5,483,163 A * | 1/1996 | Wen | G01R 33/3453 324/318 |
| 7,088,102 B1 | 8/2006 | Zens | |
| 7,106,063 B1 | 9/2006 | Zens | |
| 7,352,185 B1 | 4/2008 | Zens | |
| 7,557,578 B1 | 7/2009 | Zens | |
| 7,570,059 B2 * | 8/2009 | Greim | G01R 33/3415 324/322 |
| 8,063,639 B2 | 11/2011 | Zens | |
| 2001/0033165 A1 * | 10/2001 | Tomanek | G01R 33/341 324/318 |
| 2009/0256569 A1 * | 10/2009 | Hancu | G01R 33/34061 324/314 |
| 2010/0156414 A1 * | 6/2010 | Sakellariou | G01R 33/307 324/309 |
| 2011/0025326 A1 | 2/2011 | Zens | |
| 2014/0057792 A1 | 2/2014 | Brey | |

FOREIGN PATENT DOCUMENTS

| | | |
|---|---|---|
| WO | WO2013/108142 | 7/2013 |
| WO | WO2016179523 | 5/2016 |

OTHER PUBLICATIONS

Bowyer, P. et al., "Using magnetic 1-25 coupling to implement1H,19F,13C experiments in routine high resolution NMR probes", Journal Magnetic Resonance, vol. 261, (2015) , pp. 190-198.

Van Hecke P, et al., "Double-Tuned Resonator Designs for NMR Spectroscopy", Journal Magnetic Resonance, vol. 84, (1989), pp. 170-176.

Hoult, D.I., et al., "Use of Mutually Inductive Coupling in Probe Design", Concepts in Magnetic Resonance (Magnetic Resonance Engineering), vol. 15, (2002), pp. 262-285.

Kuhns PL et al., "Inductive coupling and tuning in NMR probes; Applications", Journal Magnetic Resonance, vol. 78, (1988), pp. 69-76.

Tang, J.A. et al., Practical aspects of liquid-state NMR with inductively coupled solenoid coils, Magnetic Resonance in Chemistry, Jul. 27, 2010, (wileyonlinelibrary.com.) DOI 10.1002/mrc.2651.

EPO Examination Report 16731648.8, regional phase in Europe of PCT/IB2016/000730, dated Apr. 24, 2018, 8 pages.

PCT Rule 43bis.1, International Search Report, PCT/JP2017/000178, dated Oct. 17, 2017, 11 pages.

Japanese Office Action for Application No. 2017-553891, dated Oct. 9, 2018, 4 pages.

English translation of Japanese Office Action for Application No. 2017-553891, dated Oct. 9, 2018, 3 pages.

* cited by examiner

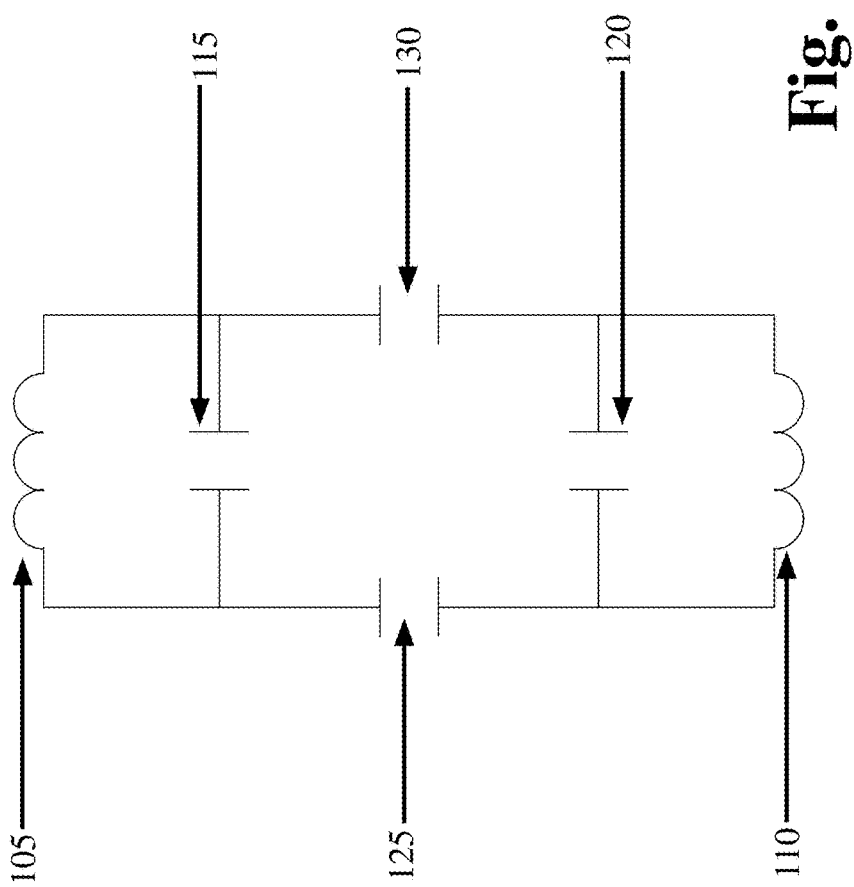

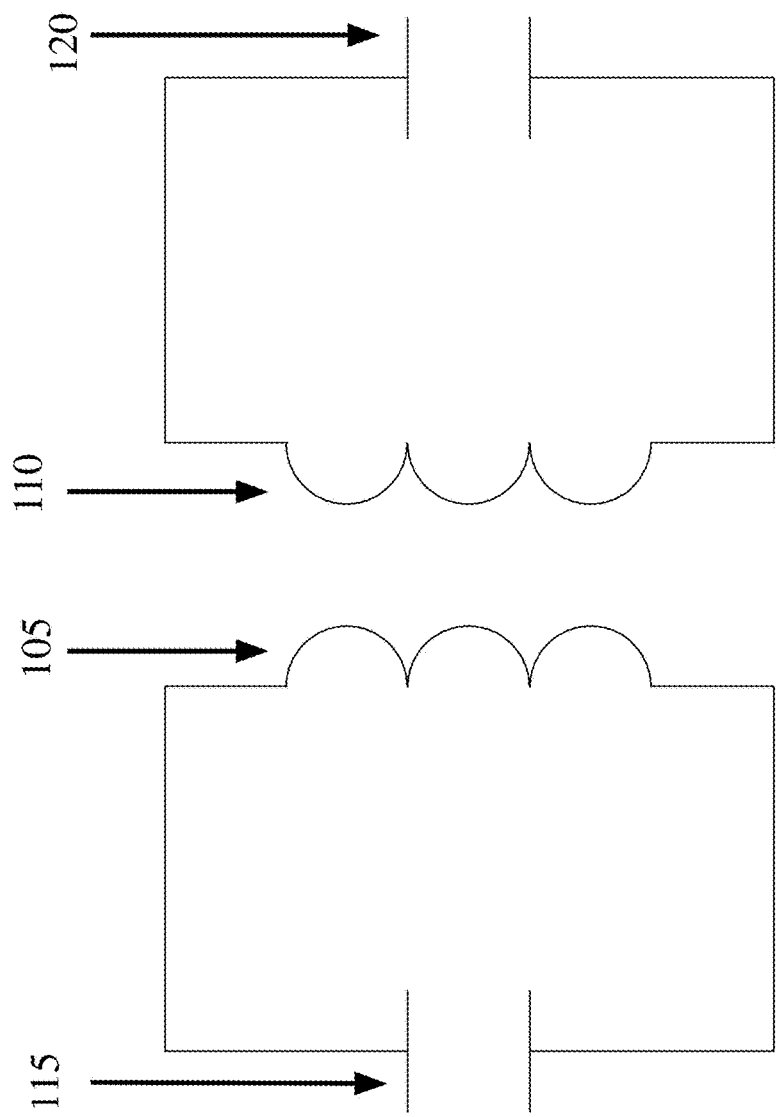

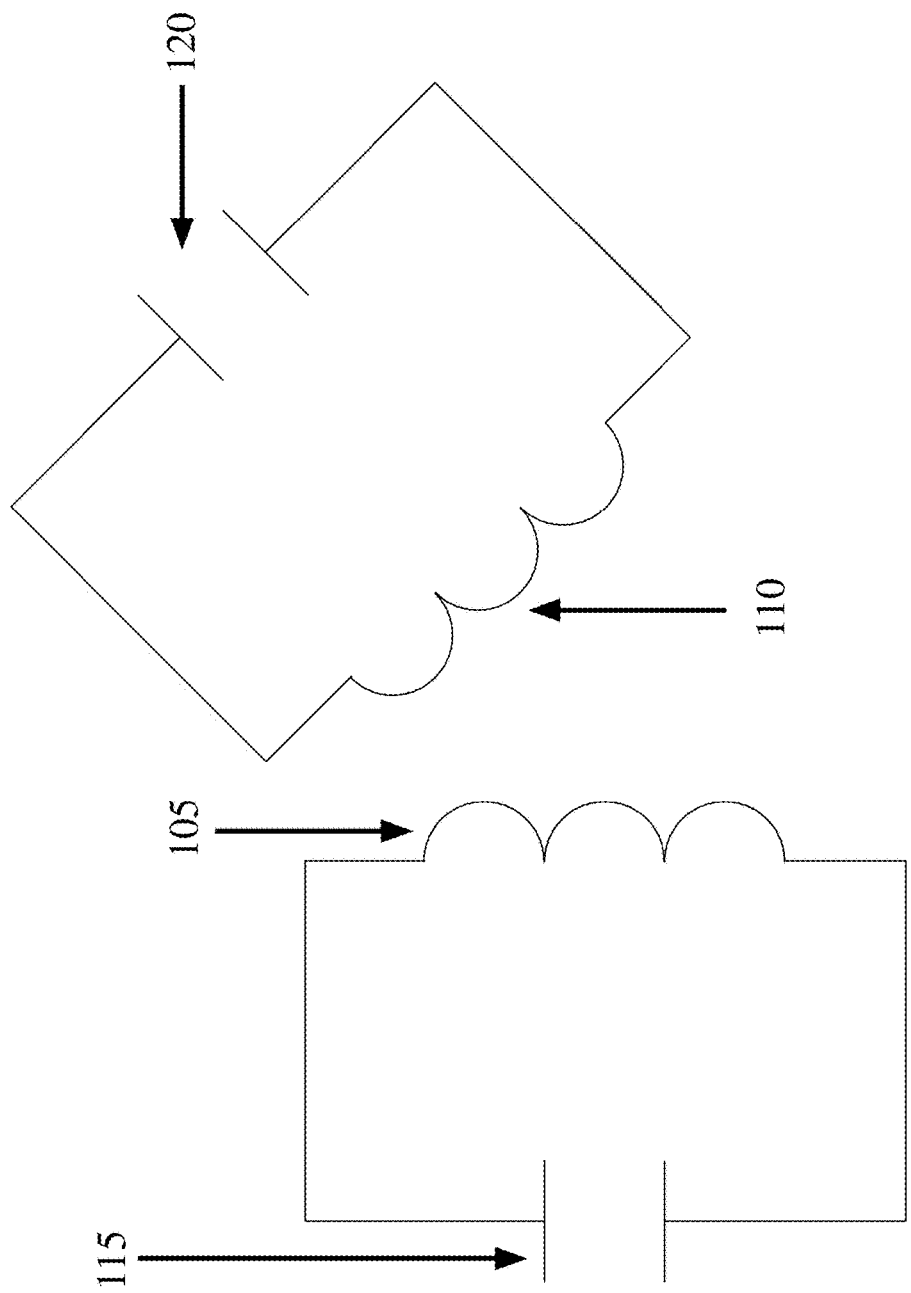

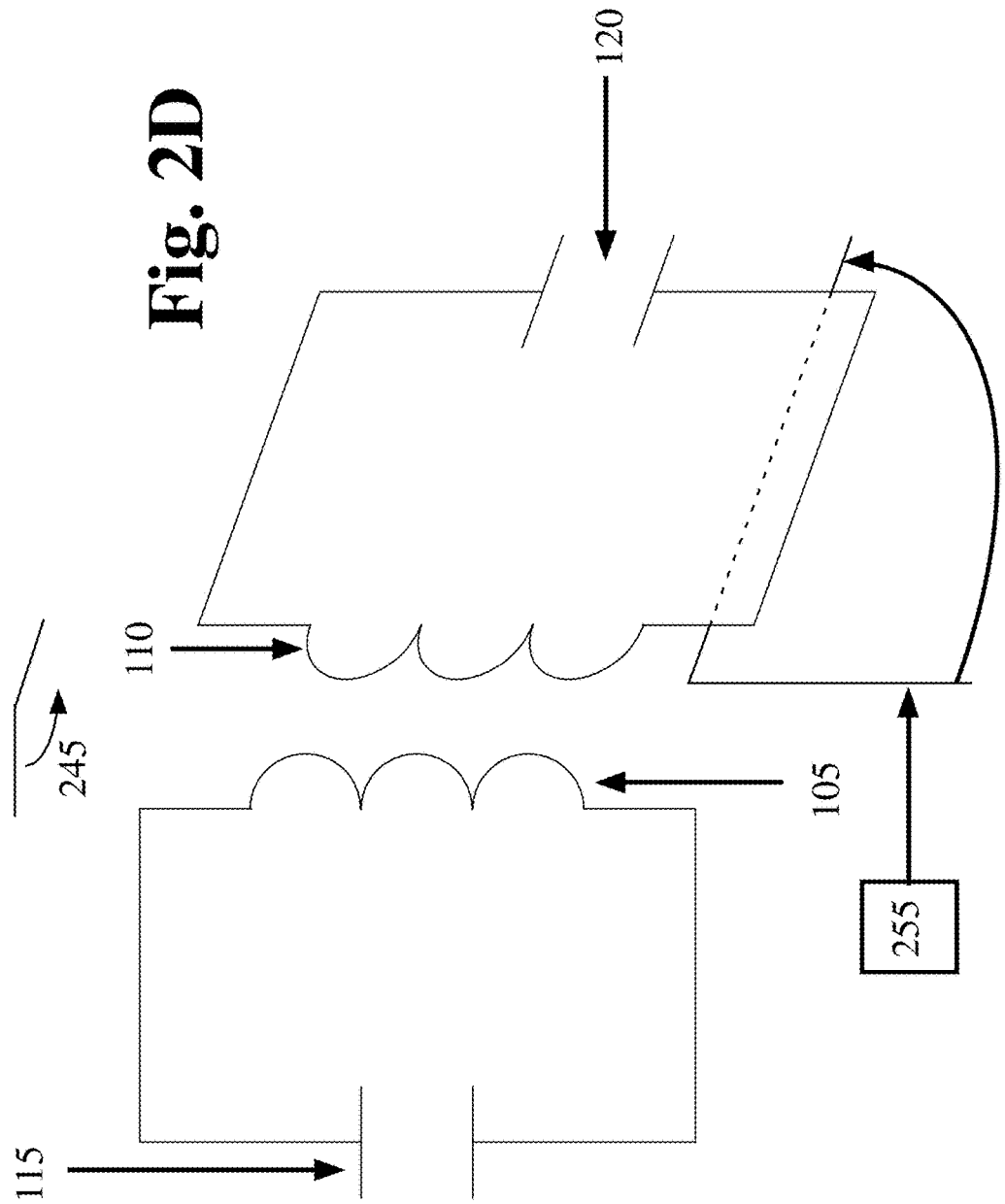

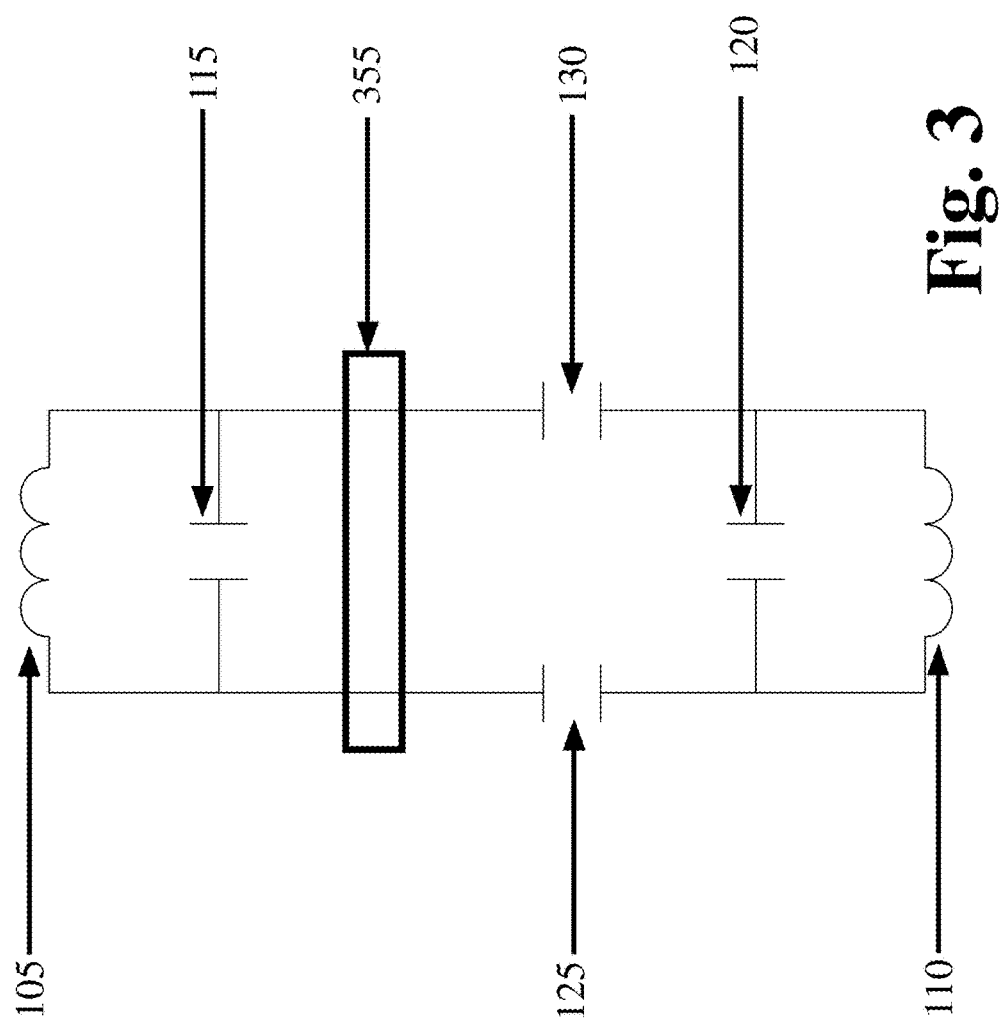

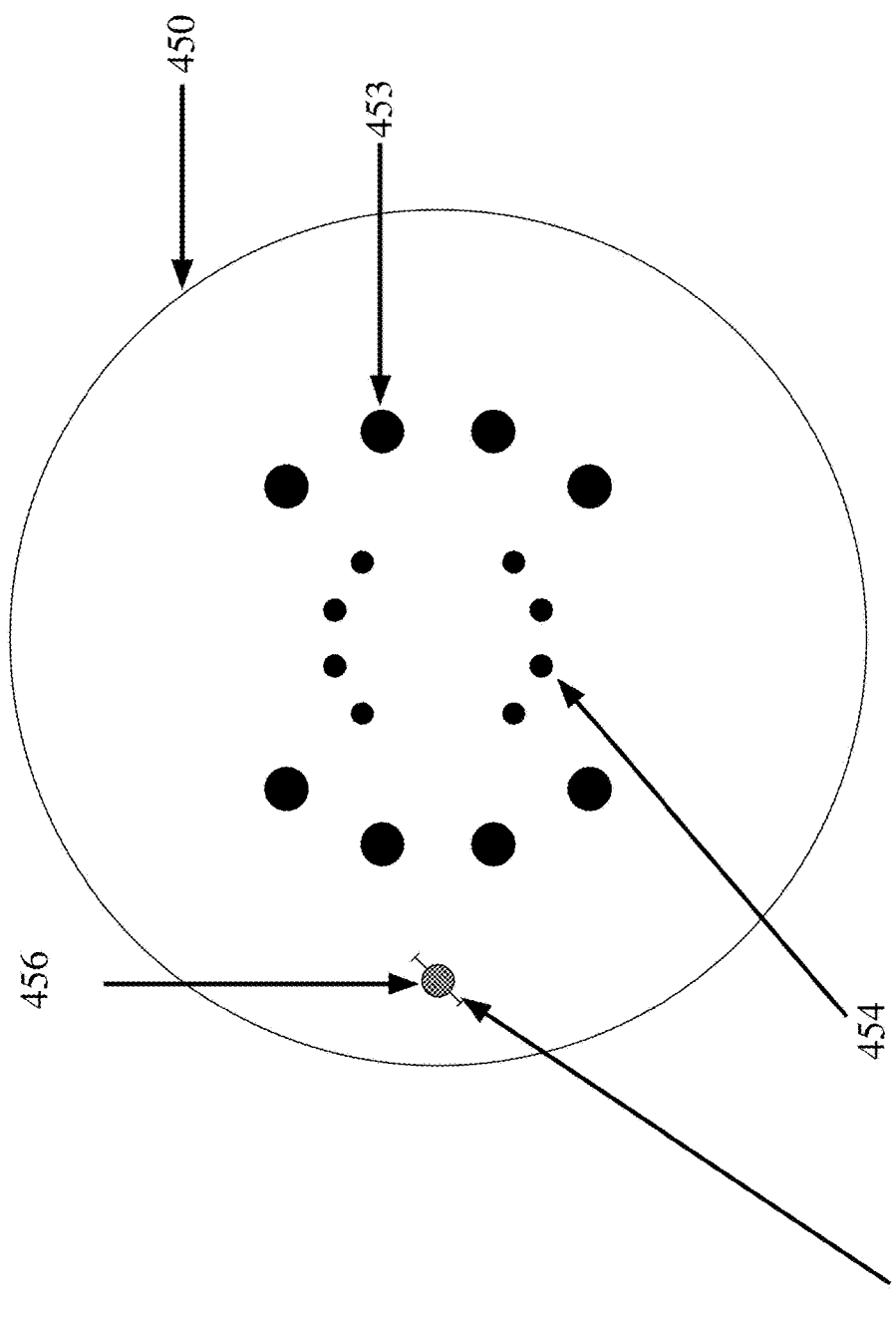

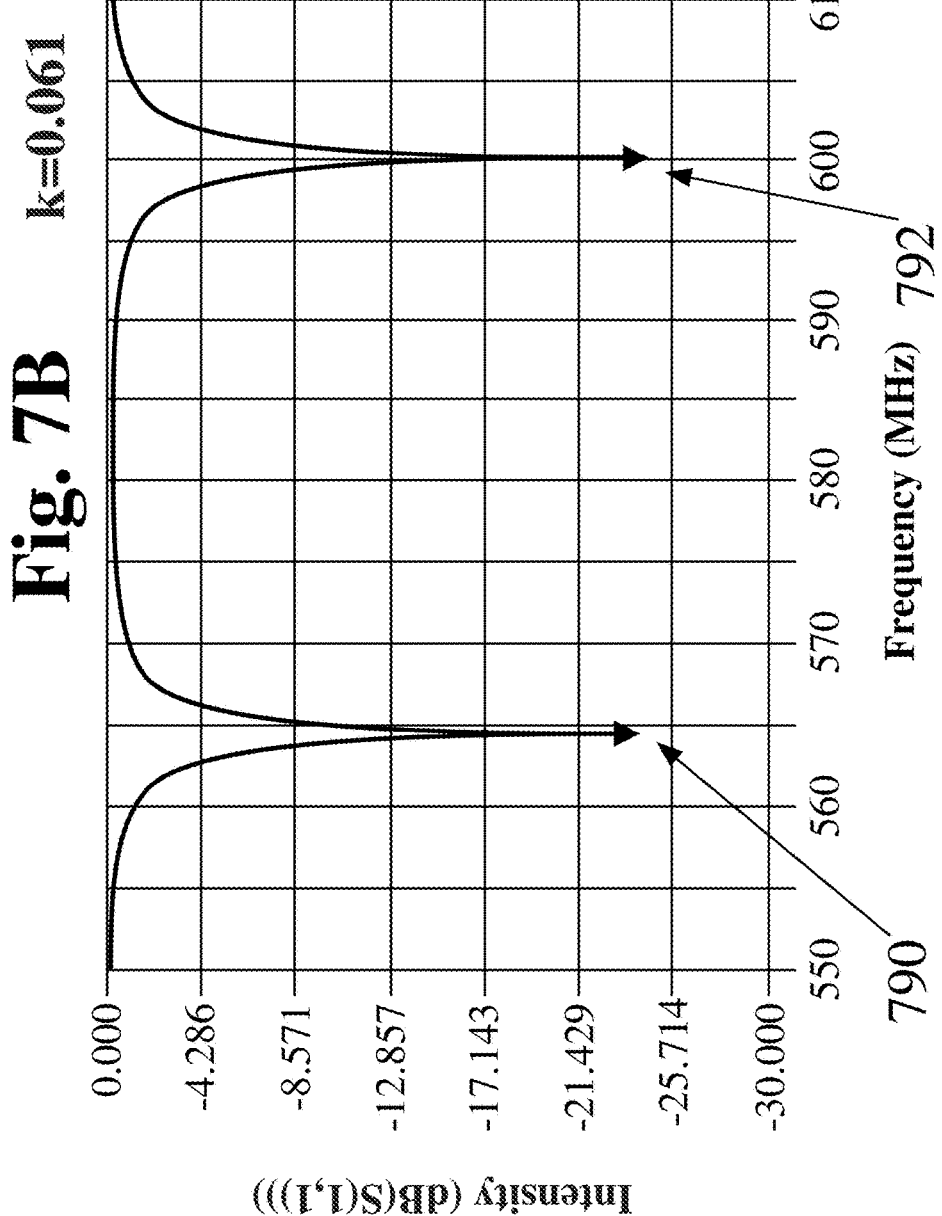

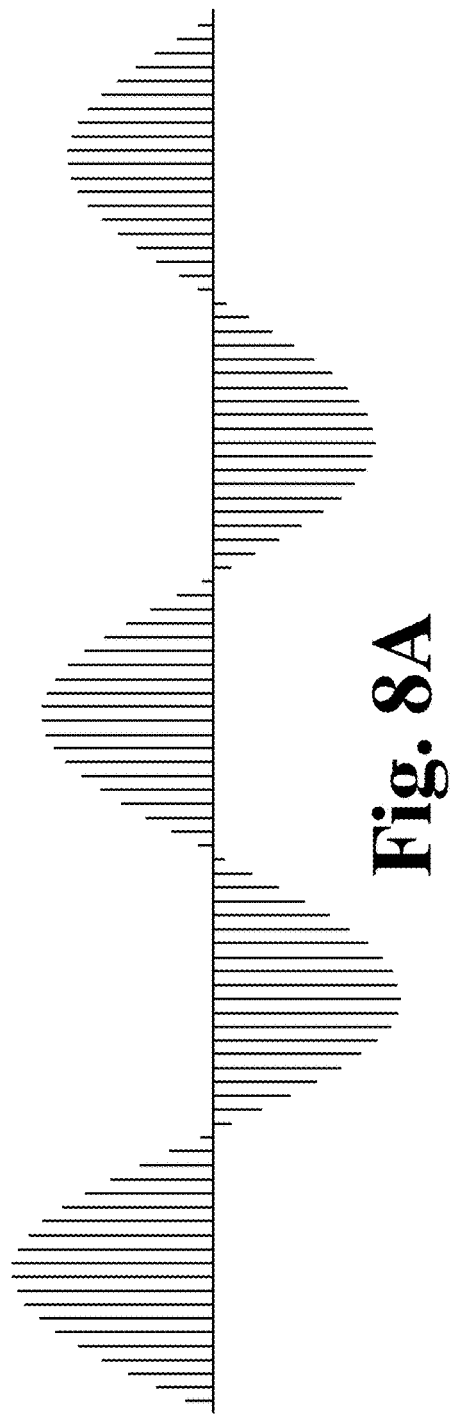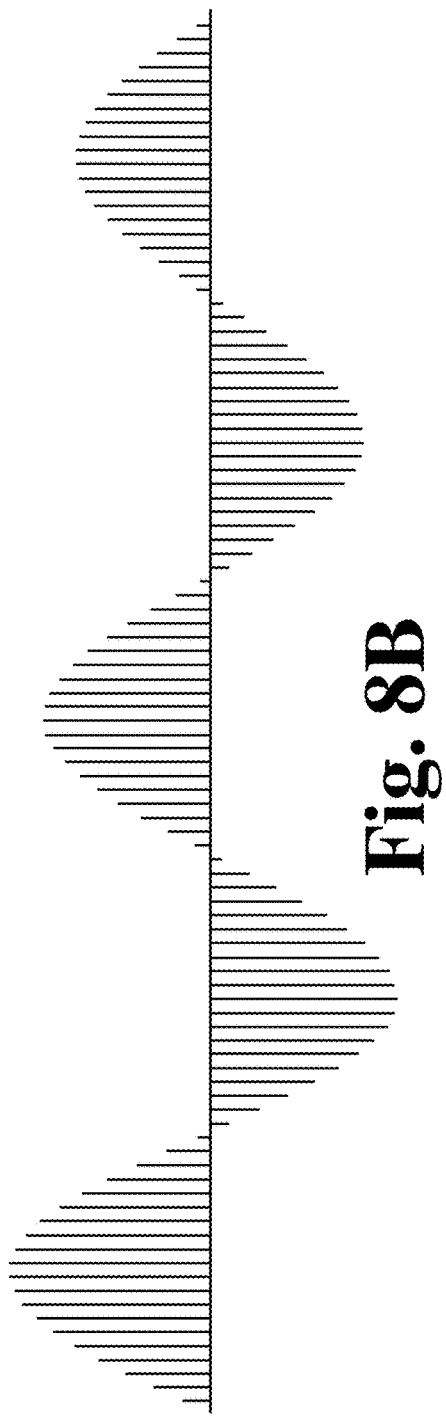

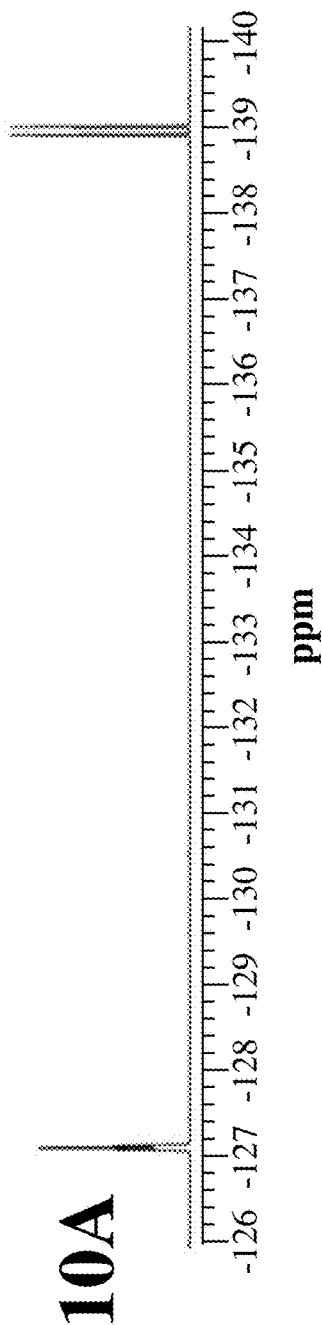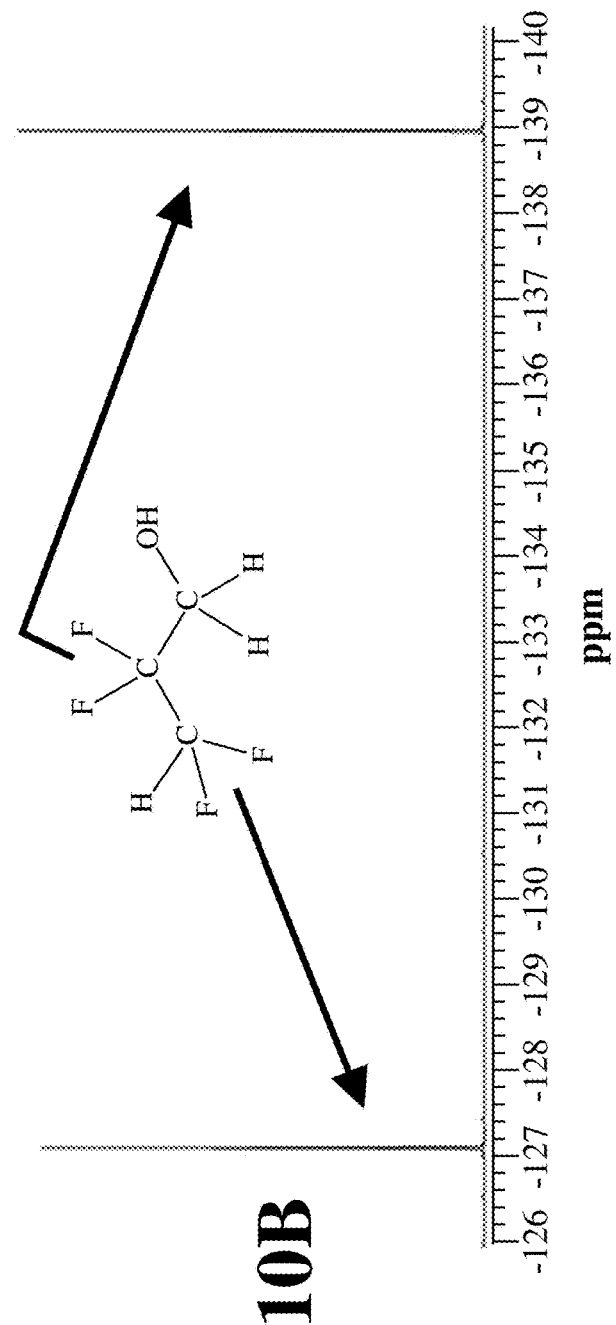
Fig. 10A
Fig. 10B

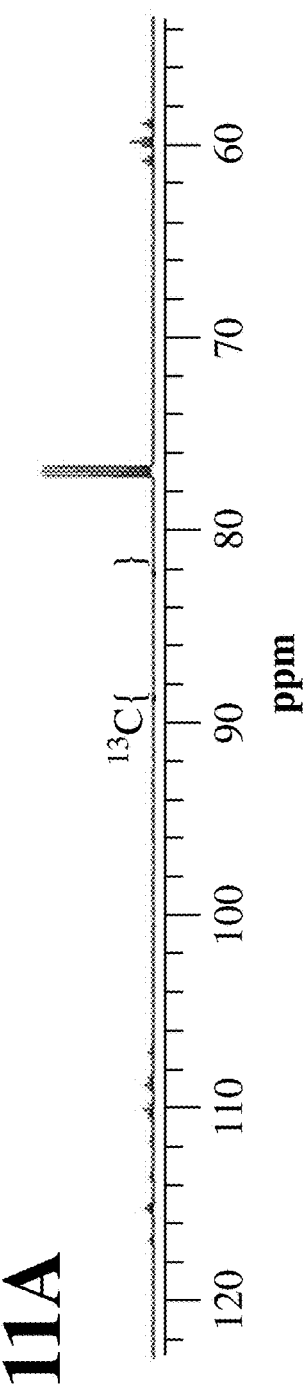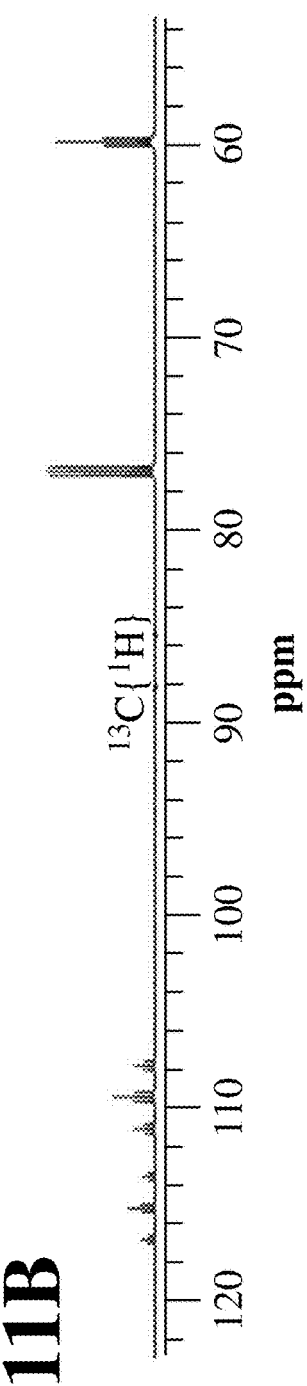
Fig. 11A
Fig. 11B

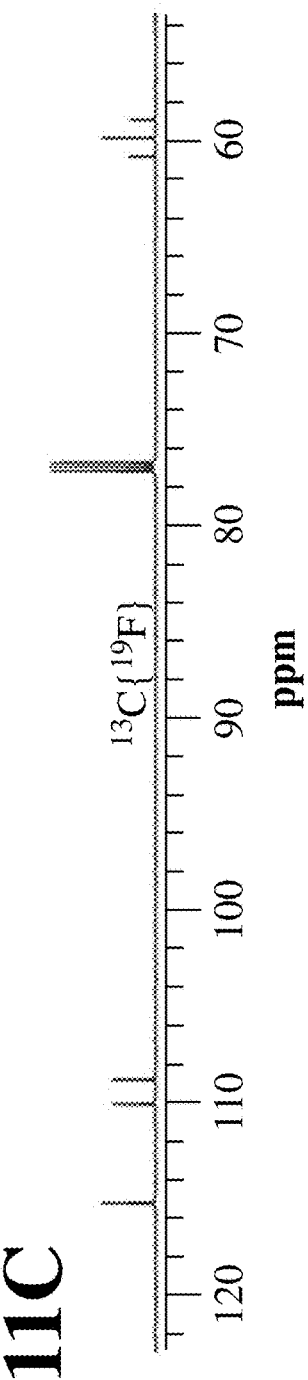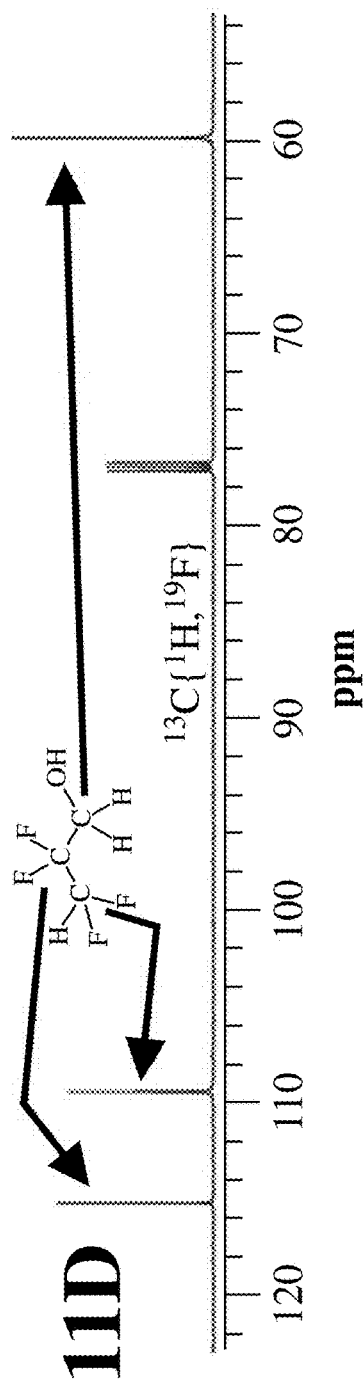

MAGNETIC COUPLING HIGH RESOLUTION NUCLEAR MAGNETIC RESOLUTION PROBE AND METHOD OF USE

FIELD OF THE INVENTION

The present invention relates to methods and devices using magnetic coupling to monitor dual nuclei in high resolution nuclear magnetic resolution probes utilizing radio frequency (RF) signals.

BACKGROUND OF THE INVENTION

Structural elucidation of a compound, whether a synthesis product or an extract from a natural source generally requires a number of analytical techniques. Infrared spectroscopy, mass spectrometry, and nuclear magnetic resonance (NMR) spectroscopy can provide extensive chemical information. NMR can provide structural information and also information on both intermolecular and intramolecular dynamics. Applications of NMR range from determination of three-dimensional structures of large proteins to the analysis of very small amounts of products from combinatorial syntheses. Furthermore, NMR is a nondestructive analytical method.

High resolution NMR probes typically have an 'inner coil' for irradiation and detection of a first nuclear species, and a second larger coil, coaxial with the inner coil, for irradiation of one or more other nuclear species. The two coils are oriented 90° with respect to each other to minimize coupling between the two coils. Capacitive coupling has previously been used to form double-tuned high resolution NMR probes for $^1H$-$^2H$, $^{13}C$-$^{15}N$ and $^1H$-$^{19}F$.

In U.S. Pat. No. 3,789,832 to Damadian a method for imaging is described in which spatial localization is achieved by means of applying a spatially inhomogeneous static magnetic field where the signal is measured in the small homogeneous region of the static field. In U.S. Pat. No. 4,301,410 to Wind et al., a method is disclosed for spin imaging solids using NMR spectroscopy by rotating the sample about an axis at a particular angle to the NMR static external magnetic field, with a magnetic field gradient with a spatial distribution which is related to the sample spinning axis is synchronously rotated with the sample. In U.S. Pat. No. 4,654,593 to Ackerman, a method for NMR imaging uses a nonmagnetic moving object positioned in the field of a RF excitation coil and a magnetic field where the object is of a low conductivity so as to be substantially transparent to electromagnetic radiation at the NMR frequency and the nonmagnetic object is subjected to periodic motion while transverse magnetization is generated, and a short duration phase-encoding magnetic field gradient pulse is applied in a specified direction to the moving nonmagnetic object, where the magnetic field gradient is turned off and a free induct ion decay signal is detected. In U.S. Pat. No. 5,227,724 to Cory et al., a method for measuring the distribution of the extent of molecular transport along two orthogonal directions, and further for measuring the anisotropy of molecular transport is disclosed. In U.S. Statutory Invention Registration. No. H1218 to Cory et al., a method of NMR imaging where spatial coupling of the sample with a receiver device is varied using pulsed magnetic field gradients and the sample is moved relative to the receiver device, or the spatial coupling of the receiver device and the sample is electronically altered, is disclosed. Kuhns, P. L. et al. describe the use of inductive coupling for series linked tuning of resonant circuits, J. Magnetic Resonance, "Inductive Coupling and Tuning in NMR Probes: Applications", 78 (1988) 69-76. Hoult, D. I. and Tomanek, B. describes the use of mutually inductive coils and investigates field strength, losses and signal to noise, "Use of Mutually Inductive Coupling in probe Design", Concepts in Magnetic Resonance, 15(4) (2002) 262-285, Wiley Periodicals, Inc.

SUMMARY OF THE INVENTION

A new problem in the NMR field is that prior art devices using capacitive coupling produce double tuned NMR probes, which do not provide sufficient sensitivity for many uses, especially for obtaining NMR spectra of complex molecules. This problem has been solved by the creation of a new type of inductive coupling coil that can provide a double resonance circuit without the disadvantages of prior art coils. Therefore, in various embodiments of the present invention, an inductive coupling coil can be used to achieve a double-tuned circuit. In various embodiments of the present invention, circuits use inductive coupling to achieve a double resonance circuit for $^1H$, $^{19}F$, $^{13}C$ (i.e., HFC) experiments where one of the three nuclei are observed and the other two decoupled or some subset of these experiments (i.e., $^1H\{^{19}F\}$ or $^{19}F\{^1H\}$).

BRIEF DESCRIPTION OF THE DRAWINGS

This invention is described with respect to specific embodiments thereof. Additional aspects can be appreciated from the Figures in which:

FIG. 1 is a schematic diagram of a Haase circuit;

FIG. 2A is a schematic diagram of magnetically coupled resonators, according to an embodiment of the invention;

FIG. 2C is a schematic diagram of magnetically coupled resonators shown in FIG. 2A decoupled by changing the orientation of one induction coil relative to the other induction coil, according to an embodiment of the invention;

FIG. 2D is a schematic diagram of magnetically coupled resonators shown in FIG. 2A decoupled by changing the orientation of one induction coil relative to the other induction coil, according to an embodiment of the invention;

FIG. 3 is a schematic diagram of a modified Haase circuit with extended leads between the sample inductor and capacitors C3a and C3b;

FIG. 4 shows a cross section view of a sample chamber where an idler coil makes approximately 45 degree angle from the uncoupled position via the rotational pivot;

FIG. 7B is a plot of the uncoupled modes for the circuit in FIG. 2, according to an embodiment of the invention;

FIG. 8A shows the RF-Homogeneity plot for the coupled version of $^1$H observed, according to an embodiment of the invention;

FIG. 8B shows the RF-Homogeneity plot for the uncoupled version of $^1$H observed, according to an embodiment of the invention;

FIG. 10A shows the NMR spectrum of $^{19}$F observed without $^1$H decoupling;

FIG. 10B shows the NMR spectrum of $^{19}$F with $^1$H decoupling;

FIG. 11A shows the NMR spectrum of $^{13}$C observed without decoupling;

FIG. 11B shows the NMR spectrum of $^{13}$C with $^1$H decoupling;

FIG. 11C shows the NMR spectrum of $^{13}$C with $^{19}$F decoupling;

FIG. 11D shows the NMR spectrum of $^{13}$C with $^1$H and $^{19}$F decoupling;

DETAILED DESCRIPTION OF THE INVENTION

Definitions

Figure 2B:
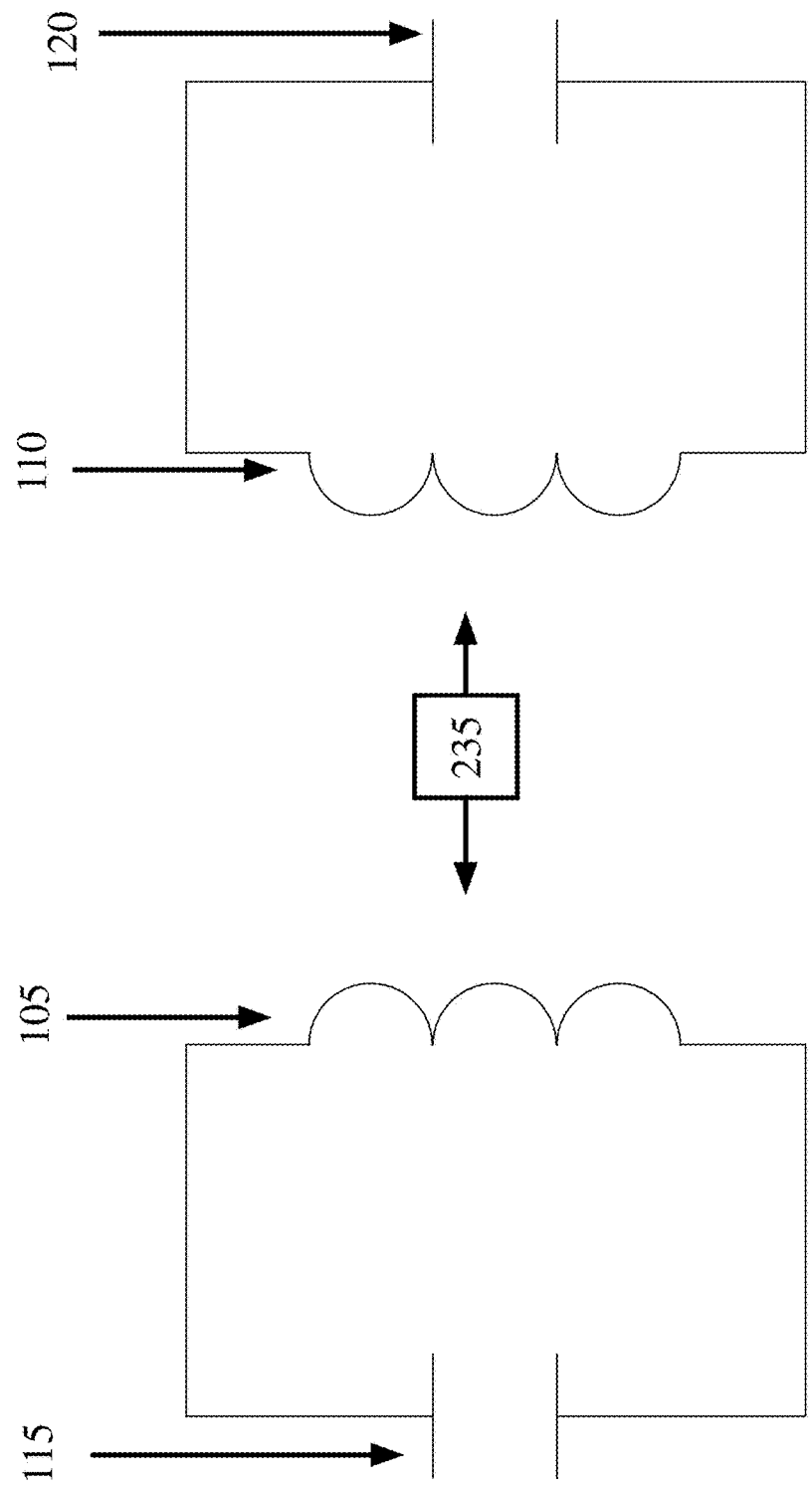
FIG. 2B is a schematic diagram of the magnetically coupled resonators shown in FIG. 2A decoupled by separating the induction coils, according to an embodiment of the invention.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

"Deployed" means attached, affixed, adhered, inserted, located or otherwise associated.

The Quality Factor (Q) is defined as the ratio of the energy stored in a component to the energy dissipated by the component. The unloaded Q ($Q_u$) is the measured Q without the load.

A "Cell" means a vessel used to contain one or more of a homogeneous or heterogeneous liquid, gas or solid sample.

A screen means two or more connected filaments, a mesh, a grid or a sheet. In various embodiments of the invention, a screen includes three or more connected filaments where at least one filament is approximately orthogonal to one other filament. A screen thickness is greater than approximately 20 micrometer and less than approximately one centimeter, where approximately is ± twenty (20) percent. A metallic screen is a screen where the filaments, mesh, grid or sheet block magnetic coupling.

A shunt means a stage that allows an inductive coil to be moved relative to another inductive coil. A shunt can be a translation shunt, see for example FIG. 2A and FIG. 2B, 235 or rotational shunt, see for example FIG. 2C or FIG. 2D, 255.

A filament means a wire with a diameter greater than approximately 20 micrometer and less than approximately one centimeter, where approximately is ± twenty (20) percent.

A metal comprises one or more elements consisting of lithium, beryllium, boron, carbon, nitrogen, oxygen, sodium, magnesium, aluminum, silicon, phosphorous, sulphur, potassium, calcium, scandium, titanium, vanadium, chromium, manganese, iron, cobalt, nickel, copper, zinc, gallium, germanium, arsenic, selenium, rubidium, strontium, yttrium, zirconium, niobium, molybdenum, technetium, ruthenium, rhodium, palladium, silver, cadmium, indium, tin, antimony, tellurium, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, thallium, lead, bismuth, polonium, francium and radium.

The word 'excitation' describes the disruption of the alignment of spins of a nuclei in a sample in a static magnetic field which occurs by applying an RF pulse at the Larmor frequency of the spins perpendicular to the magnetic field ($B_0$). The word 'performance' means the signal to noise of a circuit.

In the following description, various aspects of the present invention are described. However, it will be apparent to those skilled in the art that the present invention can be practiced with only some or all aspects of the present invention. For purposes of explanation, specific numbers, materials, and configurations are set forth to provide a thorough understanding of the present invention. However, it will be apparent to one skilled in the art that the present invention can be practiced without the specific details. In other instances, well-known features are omitted or simplified in order not to obscure the present invention.

Parts of the description are presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) can take the form of electrical, magnetic, or optical signals capable of being stored, transferred, combined, and otherwise manipulated through electrical, optical, and/or biological components of a processor and its subsystems.

Various operations are described as multiple discrete steps in turn, in a manner that is helpful in understanding the present invention; however, the order of description should not be construed as to imply that these operations are necessarily order dependent.

Various embodiments are illustrated in terms of exemplary classes and/or objects in an object-oriented programming paradigm. It will be apparent to one skilled in the art that the present invention can be practiced using any number of different classes/objects, not merely those included here for illustrative purposes.

Aspects of the invention are illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

There remain encumbrances to the employment of inductively coupled probes to the NMR technique for a variety of samples and various experimental conditions. Dual probe circuits do not utilize inductive coupling to achieve the double-tuned circuit but rather use capacitive coupling to achieve the desired tuning properties.

An example of a prior art double-tuned $^1$H, $^{19}$F (H/F) circuit is shown in FIG. 1.

Here capacitive coupling of the sample coil to the idler coil is used to produce two modes, one for $^1$H and the other for $^{19}$F, where L1 105 is the parent coil and L2 110 is the idler coil. FIG. 1 describes this basic circuit, which omits the matching components which could be either capacitive or inductive. In an embodiment of the invention, the two inductors L1 105 and L2 110 can be resonated near the halfway point between the observed frequency for $^1$H and $^{19}$F using the capacitors C1 115 and C2 120. The two coupling capacitors C3a 125 and C3b 130 are adjusted equally to create the two modes at the desired frequencies for $^1$H and $^{19}$F.

Figure 2E:
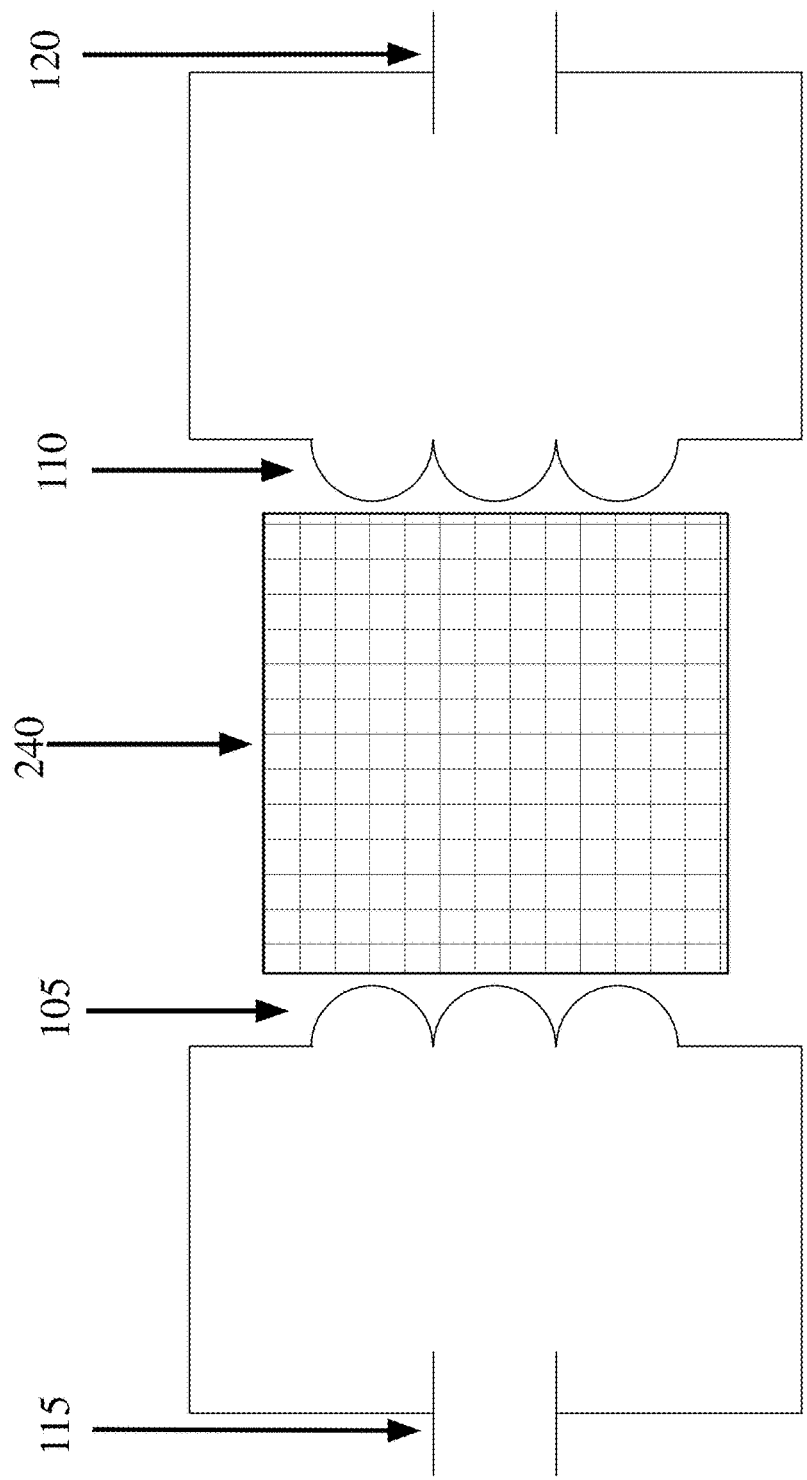
FIG. 2E is a schematic diagram of magnetically coupled resonators shown in FIG. 2A decoupled by introducing a metallic screen between the induction coils, according to an embodiment of the invention.

FIG. 2A shows a schematic diagram of an inductively coupled circuit corresponding to the capacitive coupling circuit shown in FIG. 1. FIG. 2A shows capacitors C1 115 and C2 120 and inductive coils L1 105 and L2 110, according to an embodiment of the invention. FIG. 2B is a schematic diagram of the magnetically coupled resonators shown in FIG. 2A decoupled by separating the induction coils a distance 235, according to an embodiment of the invention. FIG. 2C is a schematic diagram of magnetically coupled resonators shown in FIG. 2A decoupled by changing the orientation of one induction coil relative to the other induction coil through translation, according to an embodiment of the invention. FIG. 2D is a schematic diagram of magnetically coupled resonators shown in FIG. 2A decoupled by changing the orientation of one induction coil through rotation of the induction coil, the capacitor and the circuit, relative to the other induction coil through a degree 245, according to an embodiment of the invention. As shown in FIG. 2B, FIG. 2C, and FIG. 2D, the induction coil to be moved can be affixed or associated with a shunt 235, 255, to allow the change in position or orientation. FIG. 2E is a schematic diagram of magnetically coupled resonators shown in FIG. 2A decoupled by introducing a metallic screen 240 between the induction coils, according to an embodiment of the invention.

In various embodiments of the invention, when making the comparison between the two circuits, the same inductance for L1 and L2 can be used. In other embodiments of the invention, L1 and L2 can have different inductances. In embodiments of the invention, L1 and L2 can be chosen to have the same inductance to insure that they resonate at the same frequency. In an embodiment of the invention, the performance can be adjusted by changing the frequency of resonance. In an alternative embodiment of the invention, the performance can be adjusted by changing the unloaded inductance. In a further embodiment of the invention, the performance can be adjusted by changing the inductance. In an embodiment of the invention, L1 and L2 can be approximately 15 nanoHenries (nH), where approximately in this range corresponds with ±2 nH. The quality factor ($Q_u$) of these inductors at resonance is approximately 440. In this range, approximately means + or − five (5) percent. The capacitors used in this comparison have sufficiently low loss that the quality factor (Q) of the resonators can be determined by the resistive losses in the inductors.

For routine high resolution NMR probes, the ability to do HFC experiments is highly desirable because often in working with complex molecules containing fluorine it is necessary to determine which $^{19}$F or $^1$H is attached to a particular carbon.

Unexpectedly, it was found that the wiring could be minimized by using inductive coupling. An excellent effect was observed using inductive coupling. Using inductive coupling resulted in an advantageous effect of minimizing the amount of wiring. In a comparison of FIG. 1 and FIG. 2, one of the major advantages of inductive coupling over capacitive coupling is the lack of wires joining the two resonators. For high resolution probes the sample coil resides in a separate area of the probe away from the tuning capacitors and other circuit elements associated with the probe such as the lock and the broadband circuit of the probe. Using the capacitive coupled circuit, the leads from the sample inductor to the capacitors C3a and C3b must extend from the sample inductor area to below what is commonly called the lower insulator in the probe, a partition separating the two portions of the probe.

FIG. 3 shows the capacitors C1 115, C2 120, L1 105 and L2 110 in a modified version of FIG. 1 where a partition 355 is shown between the sample inductor and capacitors C3a 125 and C3b 130. FIG. 3 shows the leads between the sample inductor and the partition line have increased in length. The increased length of the leads has a number of negative effects. Firstly, it introduces extra stray capacitance into the circuit. Secondly, it causes additional losses associated with the additional resistance from the leads. Thirdly, the physical size of these capacitors (C3a 125 and C3b 130) in this type of circuit often interferes with the other components of the probe.

In contrast to the above constraints of the capacitive coupled circuit, inductive coupling only requires a provision to physically move the idler coil in a manner which provides for coupling and uncoupling to the sample coil. The idler coil can be rotated such that it is orthogonal to the parent coil (sample coil) or partially coupled to the parent coil. Unexpectedly, it is easier to rotate the idler coil to achieve coupling rather than move the idler coil in and out of the coupling region. An excellent effect was observed when rotating the idler coil into the coupling region to achieve inductive coupling. An advantageous effect was found by rotating the idler coil into the coupling region to affect inductive coupling.

FIG. 4 depicts a cross sectional view of the sample chamber, where the idler coil, 456, makes a 45 degree angle from the uncoupled position via the rotational pivot, 458, showing the basic orientation of the coil relative to the parent coil in the coupled mode. The larger black dots (453) indicate the vertical elements of the high frequency coil. The smaller black dots (454) indicate the vertical elements of the X coil (for observing or irradiating $^{31}$P—$^{15}$N). The $B_1$ field is contained within the circle, 450. The $B_1$ field is highly uniform at 456 (and between the Faraday screen 450 and the vertical elements of the high frequency coil, 453). In FIG. 4, the basic orientation of the idler coil relative to the parent coil can be rotated such that the idler coil can be partially coupled to the parent coil. In this position the flux emanating from the parent coil is more uniform than the flux in front of the parent coil. In various embodiments of the invention, the vertical element of the $^1$H to $^{19}$F outer coil, 453, is less sensitive to position when it is located between the Faraday Screen 450 and the vertical elements of the high frequency coil, 453. In an embodiment of the invention, the rotational pivot for the idler, 458, can be used to switch between coupled and uncoupled analysis on demand via an approximately forty five (45) degree rotation. In an embodiment of the invention, the shaft of the rotational pivot for the idler, 458, can be thin in the regions of possible physical interference and thus produce less interference with components below the lower insulator that are normally associated with the lock and X function of the probe. In an alternative embodiment of the invention, the vertical element of the X coil, 454, can be tuned to $^{13}C$.

Figure 5:
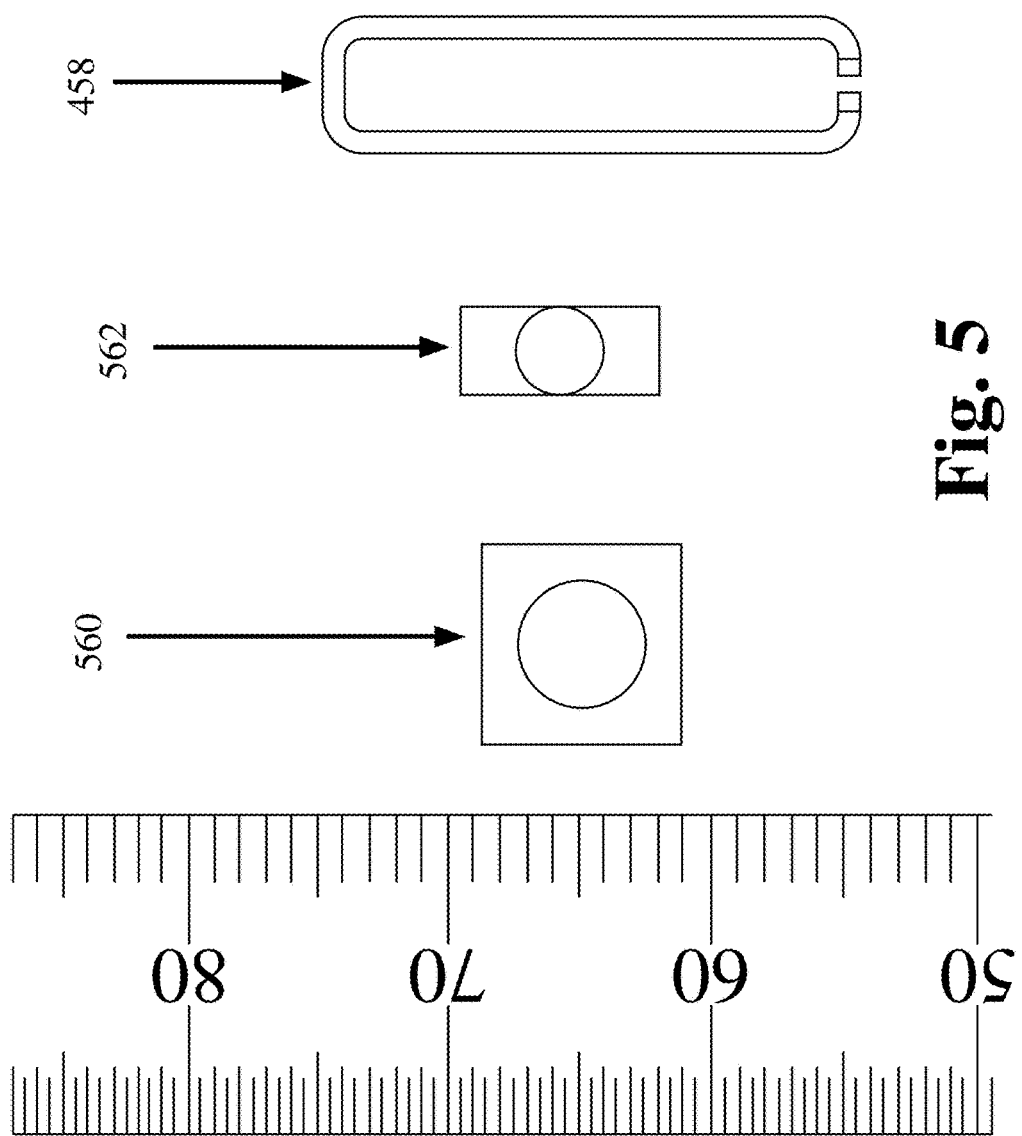
FIG. 5 is a schematic drawing of idler coil components, where after the sapphire chip capacitor is soldered to the tinned portion of an idler coil loop, the free end of the sapphire chip is mounted on a thin slotted alumina rod.

FIG. 5 is a line drawing of photograph showing the scale of the pieces that make up the idler coil in an embodiment of the invention. The idler coil 458 forms a rectangle of approximately 4 mm by 18 mm which is constructed from #18 American Wire Gauge (AWG) Oxygen-Free High thermal Conductivity (OFHC) copper wire. The sapphire chip capacitor 562 shown with solder is constructed from a Stellar sapphire chip 560 by sanding down the edges (Rotary Tool) to the final desired capacitance.

Figure 6:
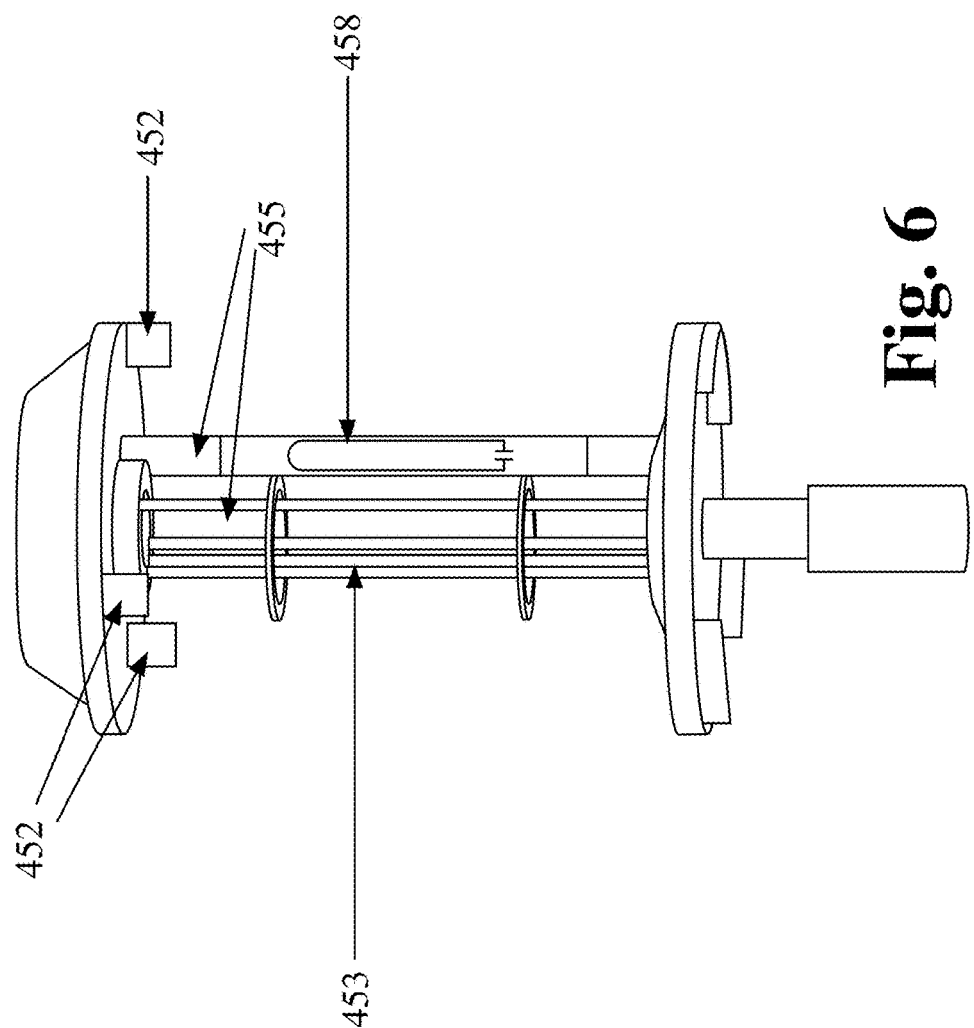
FIG. 6 is a schematic drawing of an idler coil and parent coil together, where some of the vertical elements of the parent coil have been omitted for clarity.

FIG. 6 shows a drawing of the idler coil and parent coil assembled in a probe according to an embodiment of the invention. In FIG. 6 mounting pins 452, are used to secure two vertical rods of alumina 455 to a Stellar chip cap closing the loop of the inductor, where the idler coil 458, and the vertical element of the H to F coil 453 are also shown. Unexpectedly, it was found that the idler coil 458 did not have to be susceptibility corrected for good line shape on 1% $CHCl_3$, (where peak width (Hz) at half height of $CHCl_3$ signal; peak width (Hz) of $^{13}C$ satellite of $CHCl_3$ signal; peak width (Hz) at $\frac{1}{5}^{th}$ $^{13}C$ satellite of $CHCl_3$: 0.48 Hz—50% non-spin; 4.55 Hz—0.55% non-spin; 8.83 Hz—0.11% non-spin). An excellent effect was observed where the idler coil 458 did not have to be susceptibility corrected for good line shape.

Figure 7A:
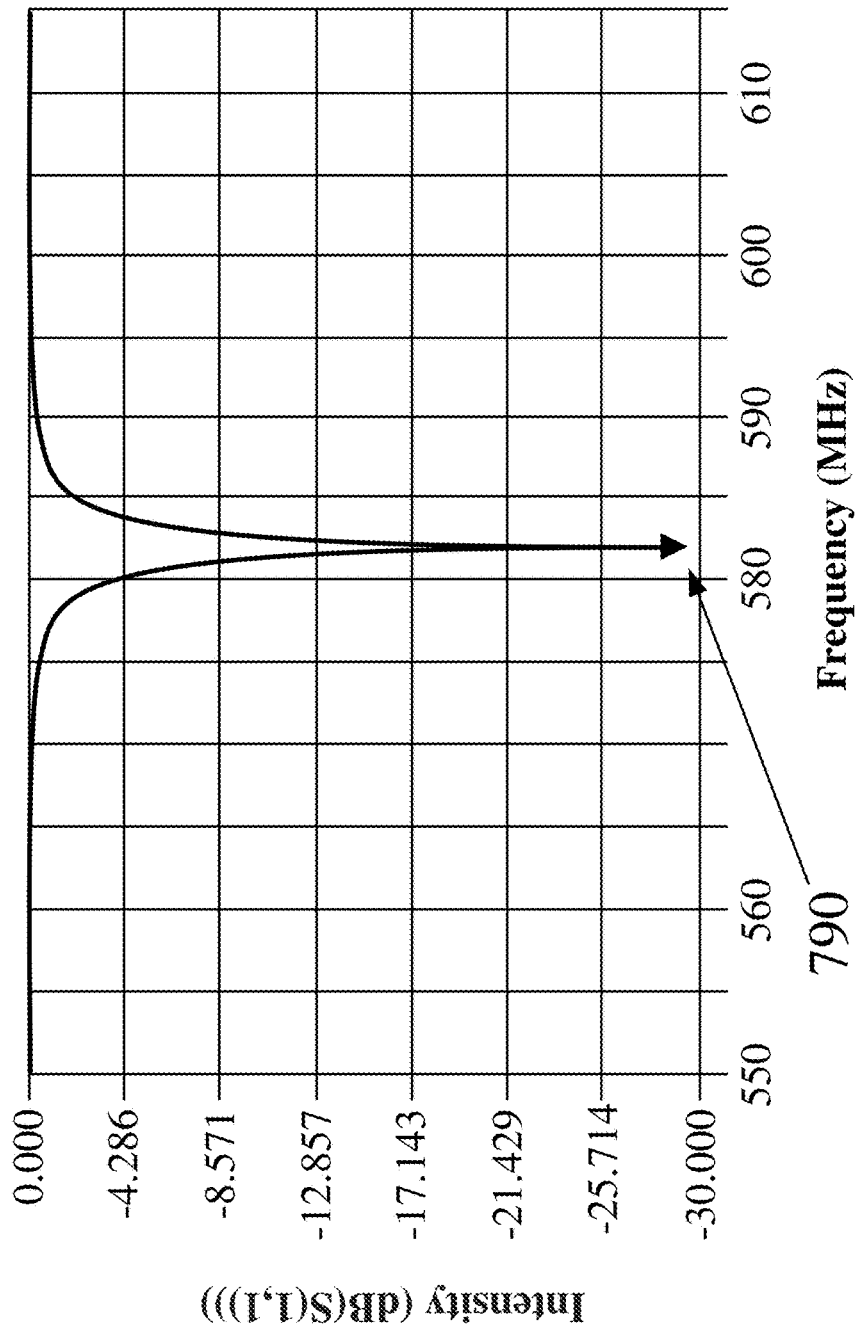
FIG. 7A is a plot of the coupled modes for the circuit in FIG. 2, according to an embodiment of the invention.

FIG. 7A is an Advance Design System plot of signal intensity versus the frequency for the S(1,1) response for the coupled mode according to an embodiment of the invention. In FIG. 7A the plot has a minimum, 790, at 582.2 MHz corresponding to 29.364 dB. FIG. 7B is an Advance Design System plot of signal intensity versus the frequency for the S(1,1) response for the uncoupled modes, where L1 and L2 are 15 nH, according to an embodiment of the invention. FIG. 7B signal intensity versus the frequency shows two well defined minimums 790, 792. FIG. 7B has a first minimum, 790, at 564.5 MHz corresponding to 24.402 dB and a second minimum, 792, at 600.0 MHz corresponding to 24.915 dB. The coupling constant between two coils (k) is given by equation (1)

$$k = M/\sqrt{(L1L2)} \quad \text{equation (1)}$$

where M is the mutual inductance between the two inductors A comparison of FIG. 7A and FIG. 7B, gives k=0.061. Unexpectedly, this is a relatively low value for the coupling constant. An excellent effect that was observed was the relatively low value for the coupling constant with the inductively coupled circuit.

Further, the efficiency of the coil was unexpectedly found to be independent of the magnitude of L2. An advantageous effect that was observed was that the efficiency of the coil was independent of the magnitude of L2. Any desired response behavior can be assured by merely establishing the natural resonance of the idler coil and then subsequently adjusting the coupling coefficient and the resonant frequency of the parent coil. These adjustments can be accomplished by rotating the idler coil and using the standard mechanism for tuning the parent resonator.

Figure 14:
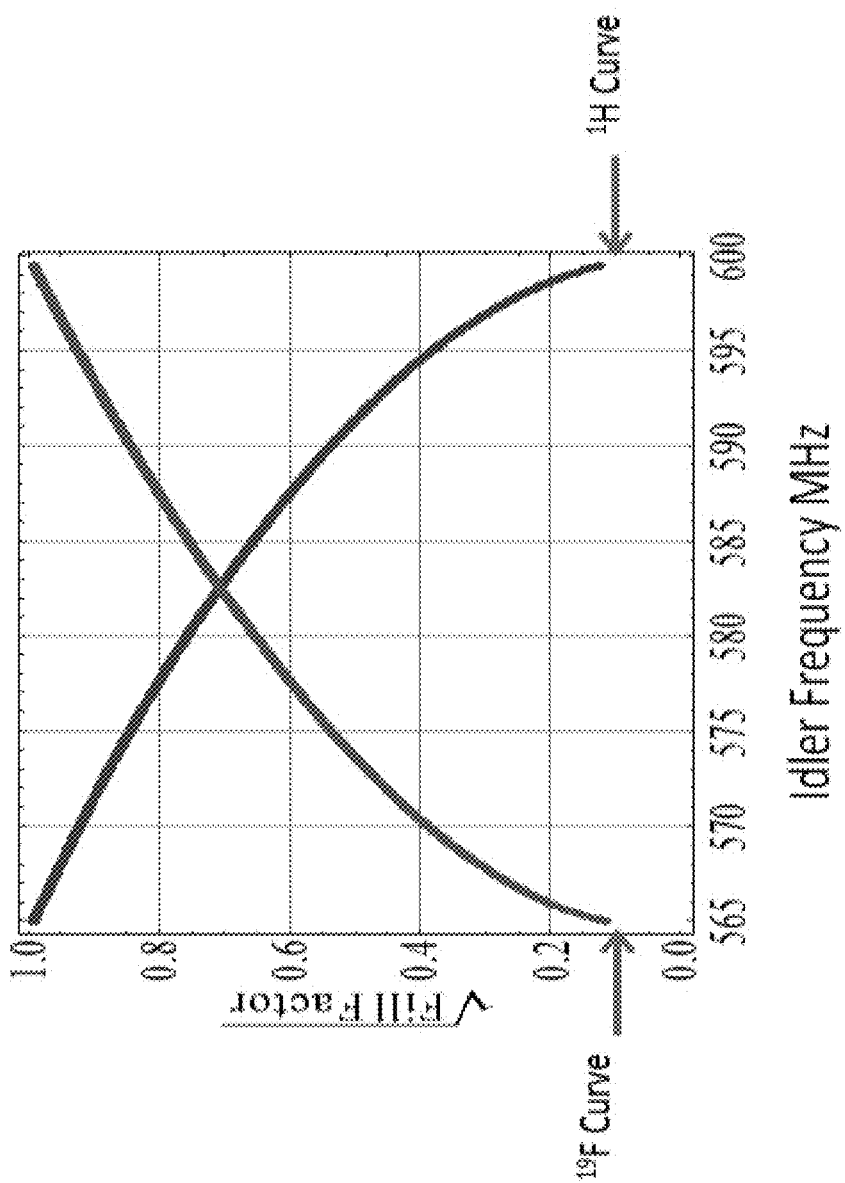
FIG. 14 is a plot of the idler frequency versus the square root of the circuit fill factor, where the resonance of the parent coil and the coupling factor are both adjusted in conjunction with the specified idler resonance to provide the required $^1$H and $^{19}$F frequencies.

FIG. 14 is a plot of the relative efficiency of $^1H$ and $^{19}F$ for a given idler frequency. To create this plot the square root of the circuit fill factor is calculated from the current in each mode. This is then used to determine the efficiency of each mode, where "efficiency" is a comparison of the square root of the circuit fill factor to unity. Both the reception signal to noise ratio and the inverse of the ninety (90) degree pulse width value are proportional to the square root of the fill factor. The relevant fill factor will be given by the product of the fill factor of the sample resonator and the circuit fill factor. Unlike the sample fill factor, the circuit fill factor does depend on frequency. However it does not depend on circuit losses or amplifier coupling. When the idler frequency is set half way between the $^{19}F$ and $^1H$ resonance the efficiency equals $1/\sqrt{2}$ for the two inductors (since $Q_{idler} \sim Q_{parent}$). Further, it can be shown that the sum of the circuit fill factor values is unity, but, as already noted, the NMR properties of interest are proportional to the square root of the circuit fill factor. From FIG. 14 the appropriate idler frequency can be determined in order to provide the desired performance ratio of the probe.

The behavior depicted in FIG. 14 is independent of the magnitude of L2. That is, any desired response behavior can be assured by merely establishing the natural resonance of the idler and then subsequently adjusting the coupling coefficient and the resonant frequency of the parent coil. These adjustments can be accomplished by rotating the idler coil and using the standard mechanism for tuning the parent resonator.

Table 1 shows comparison data for capacitive and inductive coupled coil circuits. In this comparison the X channel, Lock and matching circuits for the high frequency channel were identical except for minor component value differences in the high frequency channel. Unexpectedly, it was found an approximately 7-16% increase in performance of the inductive circuit over the capacitive circuit observed between the two circuits. An excellent effect was the approximately 7-16% increase in performance of the inductive circuit over the capacitive circuit. It is to be noted that this difference clearly favors the use of the inductive circuit over the capacitive circuit because $^{19}F$ performance is critical for a routine NMR probe due to the large chemical shift band widths. Similar simultaneously tuned H/F circuits behave in a manner similar to the Haase circuit. Here the primary fault of the Haase circuit is the loss of performance due to losses in the capacitive coupled circuit for both the coupled and uncoupled modes. The most noteworthy difference being that the inherent losses in the capacitive circuit can't be turned off in going from the coupled mode to the uncoupled mode whereas in the magnetically coupled circuit these losses can be essentially turned off. Decoupling $^{19}F$ in HSQC experiments in many cases requires over 100 KHz of decoupling capability which can lead to unwarranted amounts of power even for adiabatic decoupling sequences. It should be noted that the capacitive circuit in this example was set to favor $^1H$ over $^{19}F$. This was done primarily because the majority of users undertake $^1H$ experiments and an ~8% drop in performance makes the probe less attractive as an alternative to inductive coupling. If the capacitively coupled probe was set up for equal loss on both channels then the coupled mode performance would have been down approximately 12% on each channel as compared to the basic probe tuned to either $^1H$ or $^{19}F$. In either case, clearly the performance of the capacitive circuit is not equal to or as good as the inductive circuit for the reasons previously mentioned.

FIG. 8A shows the plot for the coupled mode of operation while observing $^1H$, according to an embodiment of the invention. FIG. 8B shows the plot for the uncoupled mode of operation while observing $^1H$, according to an embodiment of the invention. A negative effect of using magnetic coupling over capacitive coupling can be the possible degradation of the RF-homogeneity of the parent coil. In FIGS. 8A and 8B the 810/90 values are 72% for uncoupled and 67% for the coupled modes of operation. Unexpectedly, it was found that comparison of FIG. 8A and FIG. 8B indicate only a small amount of degradation and for modern pulse sequences like CRSIS II it has no measurable effect. An advantageous effect was the small amount of degradation of the inductive circuit over the capacitive circuit. That is, the RF-homogeneity for the circuit described the 810/90 value was degraded by only approximately 5%. Importantly, the idler coil has essentially no impact on the performance of the probe in the uncoupled mode.

Figure 9A:
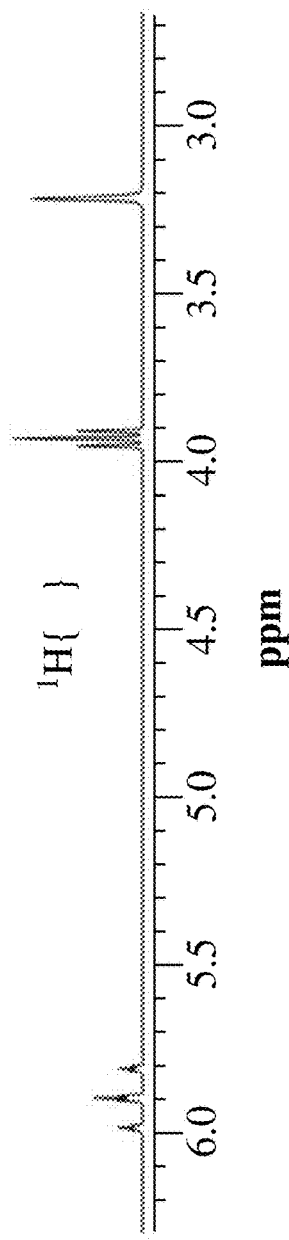
FIG. 9A shows the NMR spectrum of $^1$H observed without $^{19}$F decoupling.
Figure 9B:
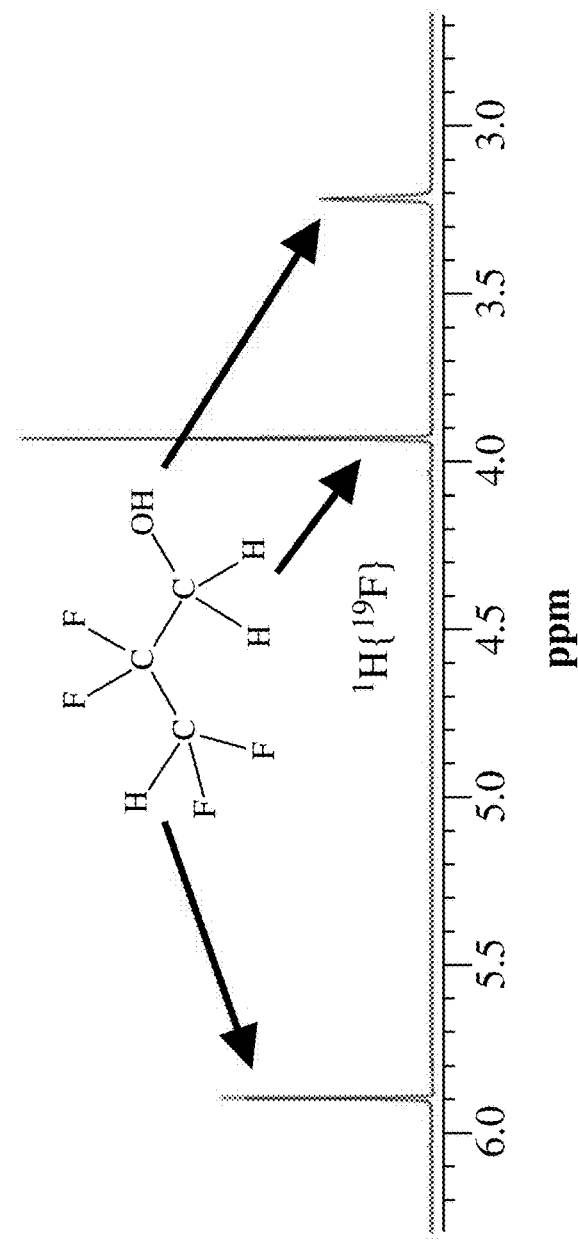
FIG. 9B shows the NMR spectrum of $^1$H with $^{19}$F decoupling.

The utility of using magnetic coupling to create a routine high resolution NMR is illustrated by the following data. It should be emphasized that the performance of the probe with or without the presence of the idler coil is the same. The addition of the idler coil allows for on-demand HFC experiments. FIG. 9A shows the NMR spectra for $^1H$ with $^{19}F$ decoupled for 2,2,3,3 tetra-Fluoro-1-propanol. FIG. 9B shows the NMR spectra for $^1H$ without $^{19}F$ decoupling for 2,2,3,3 tetra-Fluoro-1-propanol. FIG. 9B shows excellent signal to noise and excellent general sensitivity.

FIG. 10A shows the NMR spectra for $^{19}F$ with $^1H$ decoupling for 2,2,3,3 tetra-Fluoro-1-propanol. FIG. 10B shows the NMR spectra for $^{19}F$ without $^1H$ decoupling for 2,2,3,3 tetra-Fluoro-1-propanol. FIG. 10B shows excellent signal to noise and excellent general sensitivity.

FIG. 11A shows the NMR spectra for $^{13}C$ without $^1H$ or $^{19}F$ decoupling for 2,2,3,3 tetra-Fluoro-1-propanol. FIG. 11B shows the NMR spectra for $^{13}C$ with $^1H$ decoupling for 2,2,3,3 tetra-Fluoro-1-propanol. FIG. 11C shows the NMR spectra for $^{13}C$ with $^{19}F$ decoupling for 2,2,3,3 tetra-Fluoro-1-propanol. FIG. 11B and FIG. 11C show excellent signal to noise and excellent general sensitivity. FIG. 11D shows the NMR spectra for $^{13}C$ with $^1H$ and $^{19}F$ decoupling simultaneously for 2,2,3,3 tetra-Fluoro-1-propanol. Unexpectedly, FIG. 11D also shows excellent signal to noise and excellent general sensitivity. An excellent effect was the excellent signal to noise of the inductive circuit compared with the capacitive circuit. An advantageous effect was the excellent general sensitivity of the inductive circuit compared with the capacitive circuit.

Figure 12A:
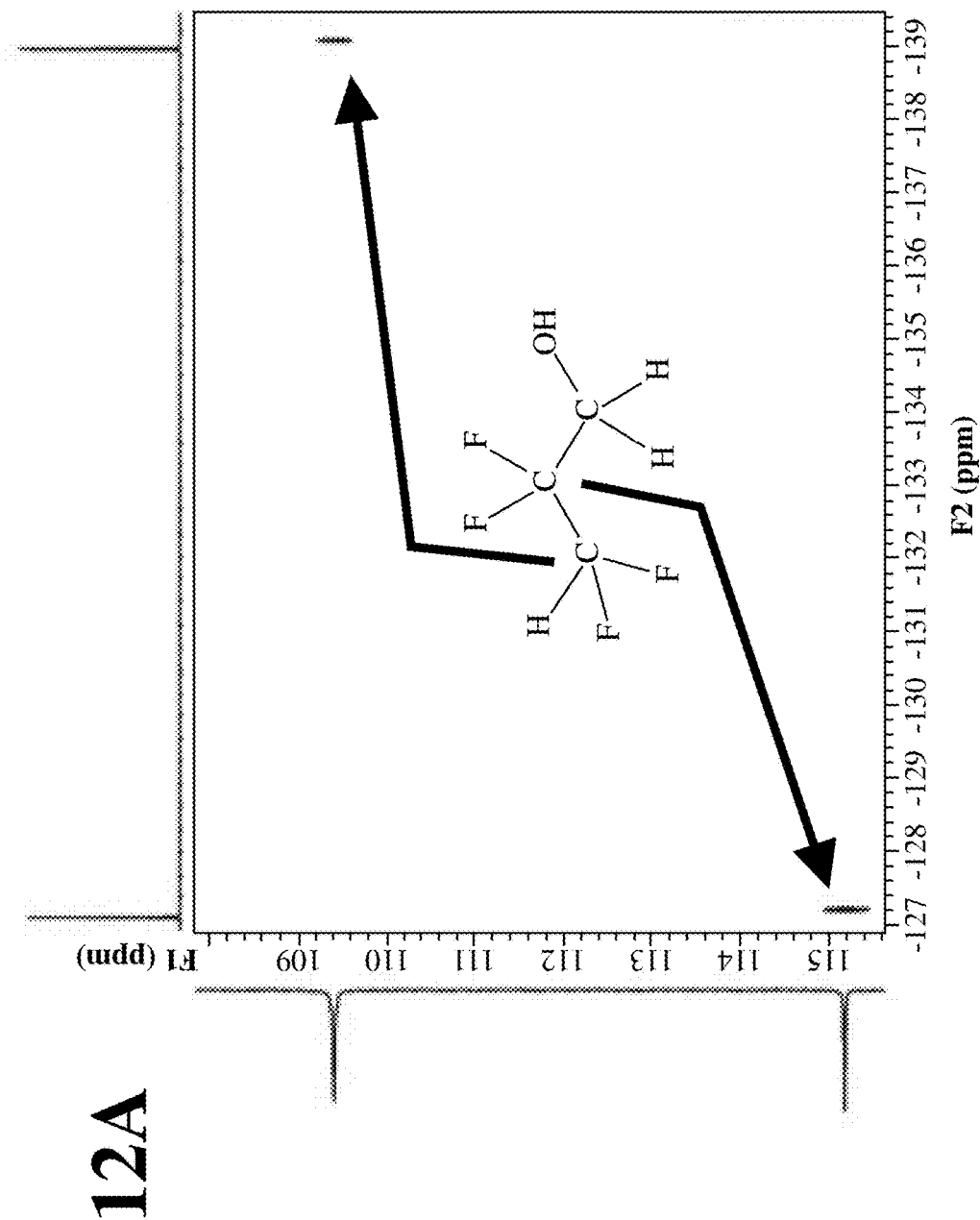
FIG. 12A shows the observed HSQC plot of $^{19}$F {$^1$H, $^{13}$C}.
Figure 12B:
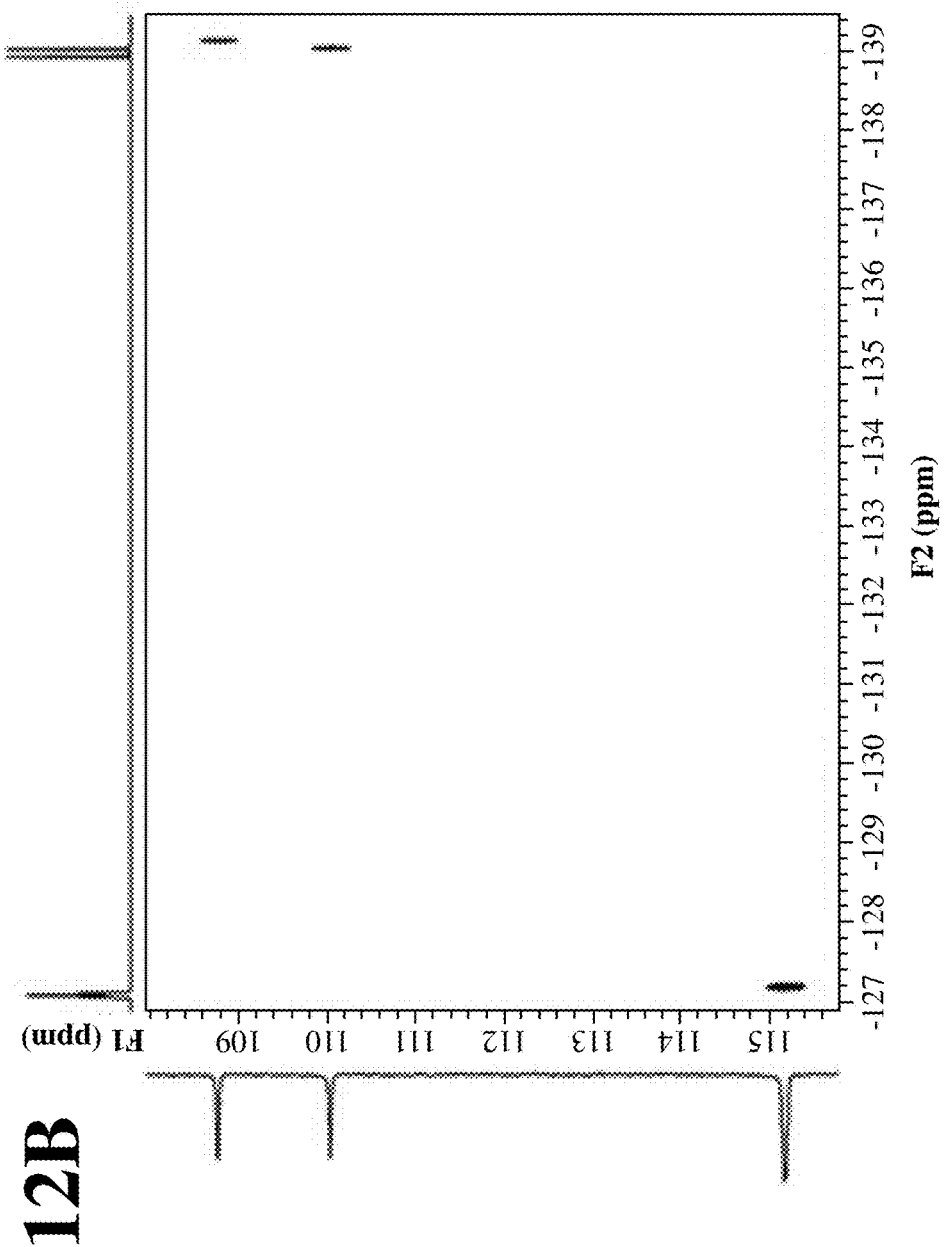
FIG. 12B shows the observed HSQC plot of $^{19}$F {$^{13}$C}.
Figure 13A:
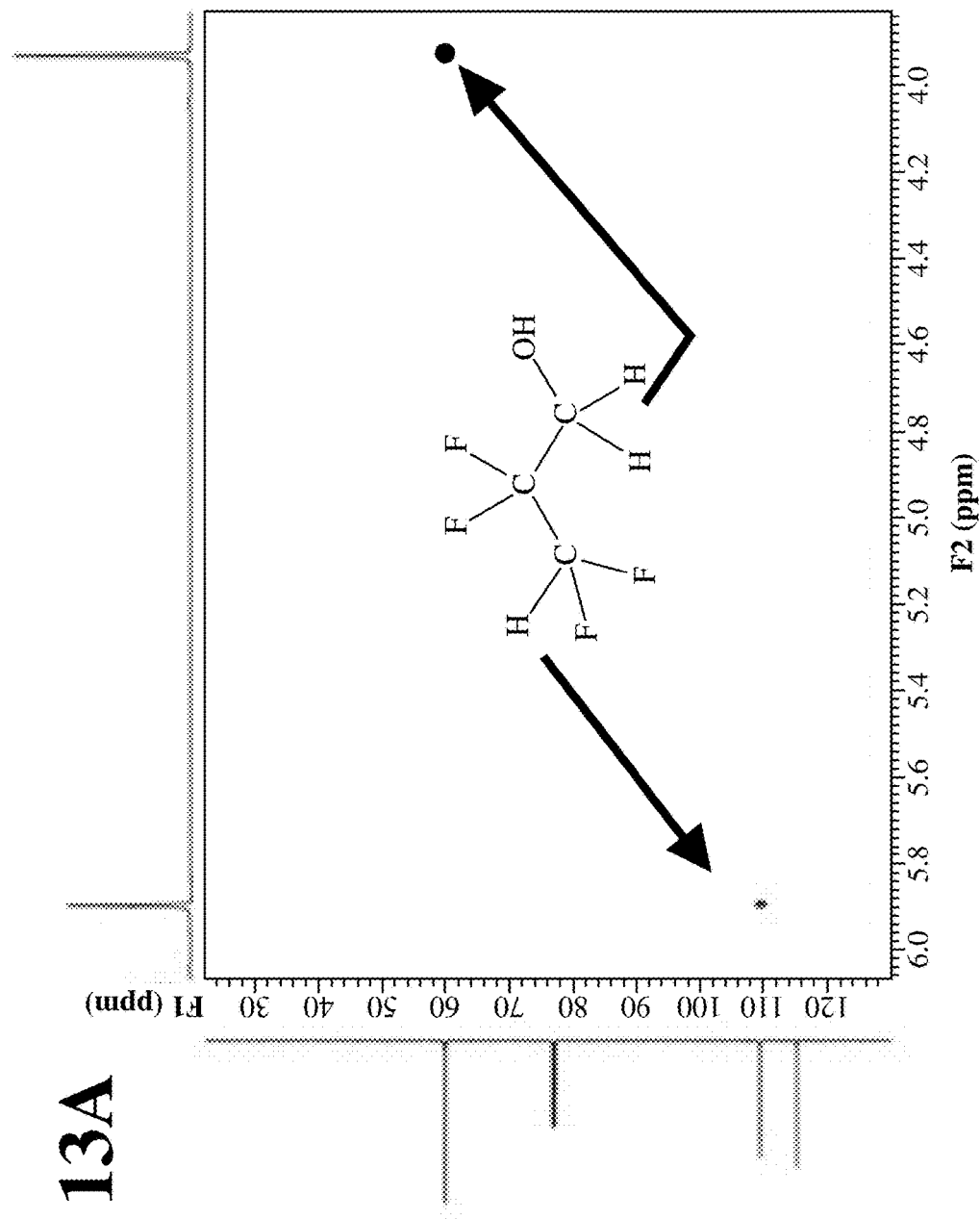
FIG. 13A shows the observed HSQC plot of $^1$H {$^{19}$F $^{13}$C}.
Figure 13B:
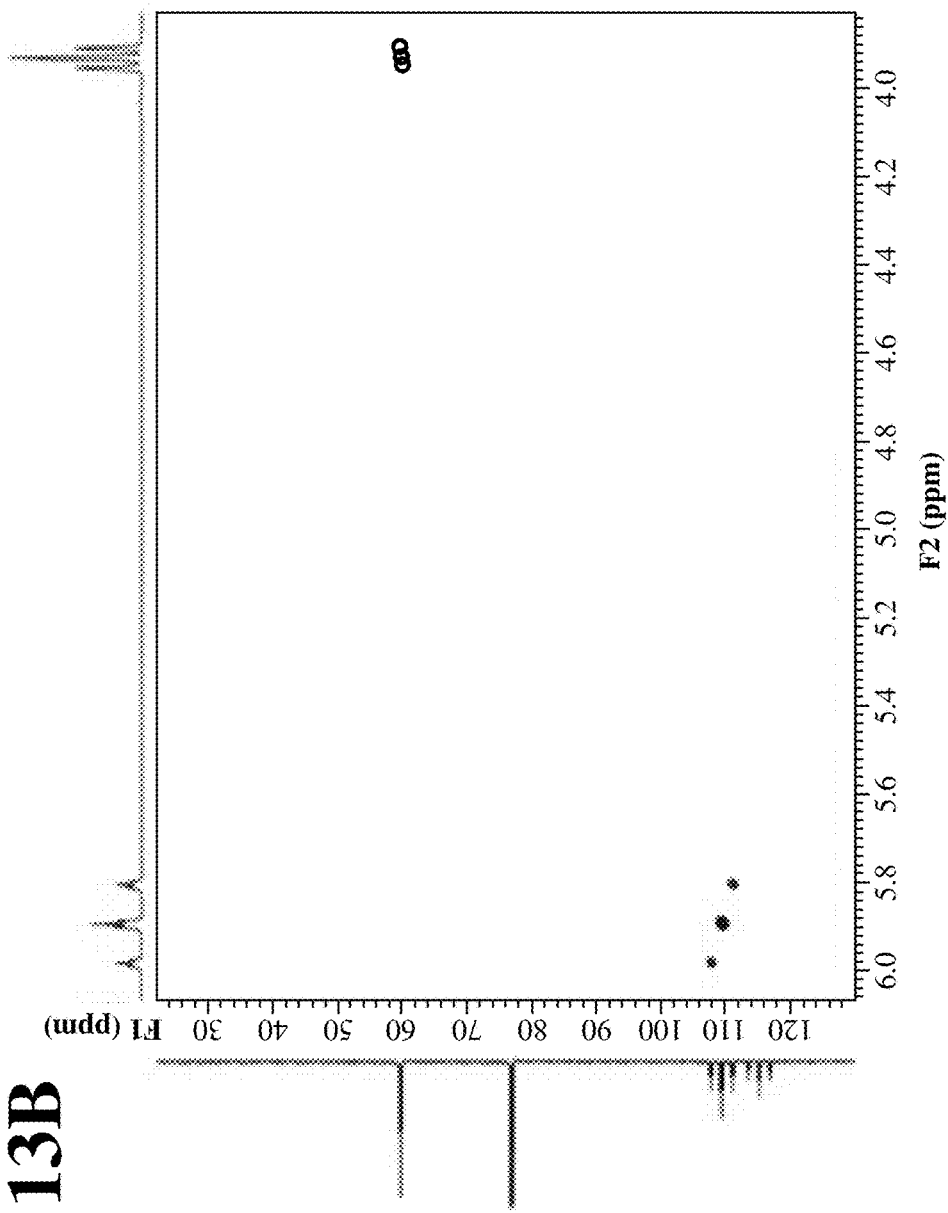
FIG. 13B shows the observed HSQC plot of $^1$H {$^{13}$C}.

FIG. 12A shows the Heteronuclear Single Quantum Correlation (HSQC) experiments of observing $^{19}F$ while decoupling $^1H$ and $^{13}C$ simultaneously for 2,2,3,3 tetra-Fluoro-1-propanol. FIG. 12B shows the HSQC experiments of observing $^{19}F$ while decoupling $^{13}C$ for 2,2,3,3 tetra-Fluoro-1-propanol. FIG. 13A shows the HSQC experiments of observing $^1H$ while decoupling $^{19}F$ and $^{13}C$ simultaneously for 2,2,3,3 tetra-Fluoro-1-propanol. FIG. 13B shows the HSQC experiments of observing $^1H$ while decoupling $^{13}C$ for 2,2,3,3 tetra-Fluoro-1-propanol.

In various embodiments of the invention, a high resolution NMR probe can routinely monitor dual nuclei to perform HFC experiments on demand using inductively coupled resonators. Unexpectedly, the performance aspects of the probe were not impacted by the use of an inductively coupled circuit. An advantageous effect was the absence of impact on the performance aspects of the probe when the inductive circuit was used compared with the capacitive circuit. In various embodiments of the invention, a high resolution NMR probe can routinely monitor dual nuclei to perform HFX experiments where X is any low-band nucleus. In various embodiments of the invention, a high resolution NMR probe can routinely monitor dual nuclei to perform analysis on a cold probe without losses to the normal dual broadband function of the probe. In various embodiments of the invention, a high resolution NMR probe can routinely monitor $^{19}F$ and another nucleus to perform fluorine chemistry.

In an embodiment of the invention, a high resolution NMR probe comprises a parent coil circuit including a parent coil adapted to detect a primary resonance mode of a nuclei, an idler coil circuit including an idler coil, wherein the idler coil is not capacitively coupled to the parent coil, wherein the idler coil is inductively coupled to the parent coil, wherein the idler coil splits the primary resonance mode, and one or both a pivot and a shunt to one or both rotate and translate to one or both couple to and decouple from the idler coil and the parent coil, wherein the parent coil is one or both rotated and translated relative to the idler coil.

In an embodiment of the invention, a high resolution NMR probe comprises a parent coil circuit including a parent coil adapted to detect a primary resonance mode of a nuclei, an idler coil circuit including an idler coil, wherein the idler coil is not capacitively coupled to the parent coil, wherein the idler coil is inductively coupled to the parent coil, wherein the idler coil splits the primary resonance mode, and one or both a pivot and a shunt to one or both rotate and translate to one or both couple to and decouple from the idler coil and the parent coil, wherein the smaller of the parent coil and the idler coil is one or both rotated and translated.

In an embodiment of the invention, a high resolution NMR probe comprises a parent coil circuit including a parent coil adapted to detect a primary resonance mode of a nuclei, an idler coil circuit including an idler coil, wherein the idler coil is not capacitively coupled to the parent coil, wherein the idler coil is inductively coupled to the parent coil, wherein the idler coil splits the primary resonance mode, wherein the frequency of the idler coil is adjusted to couple the idler coil to the parent coil.

Rather than physically moving the idler coil to decouple the idler coil and the parent coil, it is possible to change the resonance frequency of the idler coil to decouple from the parent coil. That is, the idler coil resonance frequency can be increased or decreased to decouple. Of these two approaches, lowering the idler coil frequency will result in greater losses. In an embodiment of the invention, a high resolution NMR probe comprises a parent coil circuit including a parent coil adapted to detect a primary resonance mode of a nuclei at 582.5 MHz using an approximately 14.2 Tesla 600 MHz magnet for $^1H$ observation, where $^{19}F$ resonates at approximately 564.5 MHz, an idler coil circuit including an idler coil, wherein the idler coil is not capacitively coupled to the parent coil, wherein the idler coil is inductively coupled to the parent coil, wherein the idler coil splits the primary resonance mode, wherein the lower frequency of the idler coil is adjusted to between a lower limit of approximately 620 MHz; and an upper limit of approximately 900 MHz to decouple the idler coil from the parent coil, wherein the frequency of the idler coil is adjusted to a lower limit of approximately 582 MHz; and an upper limit of approximately 583 MHz to couple the idler coil to the parent coil. When the idler coil is coupling to the parent coil, 'approximately' means±five (5) percent provided that the parent coil frequency can be adjusted to compensate for the selected idler coil frequency. When the idler coil is uncoupled with the parent coil, 'approximately' means±ten (10) percent provided that the parent coil frequency can be adjusted to compensate for the selected idler coil frequency.

In an embodiment of the invention, a high resolution NMR probe comprises a parent coil circuit including a parent coil adapted to detect a primary resonance mode of a nuclei at 582.5 MHz using an approximately 14.2 Tesla 600 MHz magnet for $^1$H observation, where $^{19}$F resonates at approximately 564.5 MHz, an idler coil circuit including an idler coil, wherein the idler coil is not capacitively coupled to the parent coil, wherein the idler coil is inductively coupled to the parent coil, wherein the idler coil splits the primary resonance mode, wherein the lower frequency of the idler coil is adjusted to between a lower limit of approximately 620 MHz; and an upper limit of approximately 900 MHz to decouple the idler coil from the parent coil, wherein the frequency of the idler coil is adjusted to a lower limit of approximately 582.25 MHz; and an upper limit of approximately 582.75 MHz to couple the idler coil to the parent coil. When the idler coil is coupling to the parent coil, 'approximately' means±five (5) percent provided that the parent coil frequency can be adjusted to compensate for the selected idler coil frequency. When the idler coil is uncoupled with the parent coil, 'approximately' means±ten (10) percent provided that the parent coil frequency can be adjusted to compensate for the selected idler coil frequency In an embodiment of the invention, a high resolution NMR probe comprises a parent coil circuit including a parent coil adapted to detect a primary resonance mode of a nuclei at 582.5 MHz using an approximately 14.2 Tesla 600 MHz magnet for $^1$H observation, where $^{19}$F resonates at approximately 564.5 MHz, an idler coil circuit including an idler coil, wherein the idler coil is not capacitively coupled to the parent coil, wherein the idler coil is inductively coupled to the parent coil, wherein the idler coil splits the primary resonance mode, wherein the lower frequency of the idler coil is adjusted to between a lower limit of approximately 400 MHz; and an upper limit of approximately 540 MHz to decouple the idler coil from the parent coil, wherein the frequency of the idler coil is adjusted to a lower limit of approximately 582.25 MHz; and an upper limit of approximately 582.75 MHz to couple the idler coil to the parent coil. When the idler coil is coupling to the parent coil, 'approximately' means±five (5) percent provided that the parent coil frequency can be adjusted to compensate for the selected idler coil frequency. When the idler coil is uncoupled with the parent coil, 'approximately' means±ten (10) percent provided that the parent coil frequency can be adjusted to compensate for the selected idler coil frequency In an embodiment of the invention, a high resolution NMR probe comprises an idler coil circuit including an idler coil and a parent coil circuit including a parent coil, where the idler coil is inductively coupled to the parent coil.

In an embodiment of the invention, a high resolution NMR probe comprises a parent coil circuit including a parent coil adapted to detect a primary resonance mode of a nuclei, an idler coil circuit including an idler coil, wherein the idler coil is not capacitively coupled to the parent coil, wherein the idler coil is inductively coupled to the parent coil, wherein the idler coil splits the primary resonance mode.

In an embodiment of the invention, a high resolution Nuclear Magnetic Resonance (NMR) probe comprises a parent coil circuit including a parent coil adapted to detect a primary resonance mode of a nuclei, an idler coil circuit including an idler coil, wherein the idler coil is inductively coupled to the parent coil, wherein the idler coil splits the primary resonance mode.

In an embodiment of the invention, a high resolution NMR probe comprises a parent coil circuit including a parent coil adapted to detect a primary resonance mode of a nuclei, an idler coil circuit including an idler coil, wherein the idler coil is not capacitively coupled to the parent coil, wherein the idler coil is inductively coupled to the parent coil, wherein the idler coil splits the primary resonance mode, and one or both a pivot and a shunt to one or both rotate and translate to one or both couple to and decouple from the idler coil and the parent coil. When the idler coil is coupling to the parent coil, 'approximately' means±five (5) percent provided that the parent coil frequency can be adjusted to compensate for the selected idler coil frequency. When the idler coil is uncoupled with the parent coil, 'approximately' means±ten (10) percent provided that the parent coil frequency can be adjusted to compensate for the selected idler coil frequency.

In an embodiment of the invention, a high resolution NMR probe comprises a parent coil circuit including a parent coil adapted to detect a primary resonance mode of a nuclei, an idler coil circuit including an idler coil, wherein the idler coil is inductively coupled to the parent coil, wherein the idler coil splits the primary resonance mode, and one or both a pivot and a shunt to one or both rotate and translate to one or both couple to and decouple from the idler coil and the parent coil.

In an embodiment of the invention, a high resolution NMR probe comprises an idler coil circuit including an idler coil and a parent coil circuit including a parent coil, where the idler coil is inductively coupled to the parent coil, further comprising a pivot, where the pivot is configured to rotate the idler coil to one or both rotate and translate to one or both couple to and decouple from the idler coil and the parent coil.

In an embodiment of the invention, a high resolution NMR probe comprises an idler coil circuit including an idler coil and a parent coil circuit including a parent coil, where the idler coil is inductively coupled to the parent coil, further comprising a shunt where the shunt is configured to rotate the idler coil to one or both rotate and translate one or both couple to and decouple from the idler coil and the parent coil.

In an embodiment of the invention, a high resolution NMR probe comprises an idler coil circuit including an idler coil and a parent coil circuit including a parent coil, where the idler coil is inductively coupled to the parent coil, further comprising a shunt where the shunt is configured to move the idler coil to one or both 'couple to' and 'decouple from' the idler coil and the parent coil.

In an embodiment of the invention, a high resolution NMR probe comprises an idler coil circuit including an idler coil and a parent coil circuit including a parent coil, where the idler coil is inductively coupled to the parent coil, further comprising a shunt where the shunt is configured to translate the parent coil to one or both 'couple to' and 'decouple from' the idler coil and the parent coil.

In an embodiment of the invention, a high resolution NMR probe comprises an idler coil circuit including an idler coil, a parent coil circuit including a parent coil, where the idler coil is inductively coupled to the parent coil, and a pivot, where the pivot is configured to orient the idler coil relative to the parent coil to one or both 'couple to' and 'decouple from' the idler coil and the parent coil.

In an embodiment of the invention, a high resolution NMR probe comprises an idler coil circuit including an idler coil and a parent coil circuit including a parent coil, where the idler coil is inductively coupled to the parent coil, further comprising a shunt where the shunt is configured to translate the idler coil to one or both 'couple to' and 'decouple from' the idler coil and the parent coil.

In an embodiment of the invention, a high resolution NMR probe comprises an idler coil circuit including an idler coil, a parent coil circuit including a parent coil, where the idler coil is inductively coupled to the parent coil, a pivot, where the pivot is configured to orient the idler coil relative to the parent coil to one or both 'couple to' and 'decouple from' the idler coil and the parent coil, and a shunt where the shunt is configured to translate the idler coil to one or both 'couple to' and 'decouple from' the idler coil and the parent coil.

In an embodiment of the invention, a high resolution NMR probe comprises an idler coil circuit including an idler coil and a parent coil circuit including a parent coil, where the idler coil is inductively coupled to the parent coil, further comprising a metallic screen where the metallic screen can be inserted between the idler coil from the parent coil to couple or decouple the idler coil from the parent coil.

In an embodiment of the invention, a high resolution NMR probe comprises an idler coil circuit including an idler coil and a parent coil circuit including a parent coil, where the idler coil is inductively coupled to the parent coil, further comprising a metallic screen where the metallic screen can be inserted between the idler coil from the parent coil to couple or decouple the idler coil from the parent coil, further comprising one or both a shunt and a pivot where the shunt or the pivot is adapted to insert the metallic screen between the idler coil from the parent coil.

In an embodiment of the invention, a high resolution NMR probe comprises an idler coil circuit including an idler coil and a parent coil circuit including a parent coil, where the idler coil is inductively coupled to the parent coil, where the idler coil has a quality factor ($Q_u$) at resonance between a lower limit of approximately 430 and an upper limit of approximately 450.

In an embodiment of the invention, a NMR system comprising a high resolution NMR probe including an idler coil circuit including an idler coil and a parent coil circuit including a parent coil, where the idler coil is inductively coupled to the parent coil, further comprising a metallic screen where the metallic screen can be inserted between the idler coil from the parent coil to couple or decouple the idler coil from the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil and a parent coil circuit comprising a parent coil, where the idler coil is inductively coupled to the parent coil, and moving the idler coil relative to the parent coil to one or both 'couple to' and 'decouple from' the idler coil and the parent coil to obtain a NMR spectrum of two or more nuclei of the sample.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil and a parent coil circuit comprising a parent coil, where the idler coil is inductively coupled to the parent coil, introducing the NMR probe into a magnetic field, and moving the idler coil relative to the parent coil to one or both 'couple to' and 'decouple from' the idler coil and the parent coil to obtain a NMR spectrum of two or more nuclei of the sample.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil and a parent coil circuit comprising a parent coil, where the idler coil is inductively coupled to the parent coil, introducing the NMR probe into a magnetic field, exciting the sample, and moving the idler coil relative to the parent coil to one or both 'couple to' and 'decouple from' the idler coil and the parent coil to obtain a NMR spectrum of two or more nuclei of the sample.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil, a parent coil circuit comprising a parent coil and a pivot, where the idler coil is inductively coupled to the parent coil, and moving the idler coil relative to the parent coil to one or both 'couple to' and 'decouple from' the idler coil and the parent coil to obtain a NMR spectrum of two or more nuclei of the sample, further comprising rotating the idler coil about the pivot relative to the parent coil to one or both 'couple to' and 'decouple from' the idler coil and the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil, a parent coil circuit comprising a parent coil and a pivot, where the idler coil is inductively coupled to the parent coil, and moving the idler coil relative to the parent coil to one or both 'couple to' and 'decouple from' the idler coil and the parent coil to obtain a NMR spectrum of two or more nuclei of the sample, further comprising rotating the idler coil about the pivot relative to the parent coil to one or both 'couple to' and 'decouple from' the idler coil and the parent coil, where rotation moves the idler coil into an orthogonal position relative to the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil, a parent coil circuit comprising a parent coil and a pivot, where the idler coil is inductively coupled to the parent coil, and moving the idler coil relative to the parent coil to one or both 'couple to' and 'decouple from' the idler coil and the parent coil to obtain a NMR spectrum of two or more nuclei of the sample, further comprising rotating the idler coil about the pivot relative to the parent coil to one or both 'couple to' and 'decouple from' the idler coil and the parent coil, where rotation moves the idler coil into an orthogonal position relative to the parent coil, where the idler coil is rotated out of an orthogonal position relative to the parent coil to couple the idler coil with the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil and a parent coil circuit comprising a parent coil, where the idler coil is inductively coupled to the parent coil, and moving the idler coil relative to the parent coil to one or both 'couple to' and 'decouple from' the idler coil and the parent coil to obtain a NMR spectrum of two or more nuclei of the sample, further comprising moving the idler coil away from the parent coil to decouple the idler coil from the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil and a parent coil circuit comprising a parent coil, where the idler coil is inductively coupled to the parent coil, and moving the idler coil relative to the parent coil to one or both 'couple to' and 'decouple from' the idler coil and the parent coil to obtain a NMR spectrum of two or more nuclei of the sample, further comprising moving the parent coil away from the idler coil to decouple the idler coil from the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil and a parent coil circuit comprising a parent coil, where the idler coil is inductively coupled to the parent coil, and moving the idler coil relative to the parent coil to one or both 'couple to' and 'decouple from' the idler coil and the parent coil to obtain a NMR spectrum of two or more nuclei of the sample, further comprising orienting the parent coil away from the idler coil to decouple the idler coil from the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil and a parent coil circuit comprising a parent coil, where the idler coil is inductively coupled to the parent coil, and moving the idler coil relative to the parent coil to one or both 'couple to' and 'decouple from' the idler coil and the parent coil to obtain a NMR spectrum of two or more nuclei of the sample, further comprising inserting a metallic screen between the parent coil and the idler coil to decouple the idler coil from the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil, a parent coil circuit comprising a parent coil and a pivot, where the idler coil is inductively coupled to the parent coil, introducing the NMR probe into a magnetic field, exciting the sample, and moving the idler coil relative to the parent coil to one or both 'couple to' and 'decouple from' the idler coil and the parent coil to obtain a NMR spectrum of two or more nuclei of the sample, further comprising rotating the idler coil about the pivot relative to the parent coil to one or both 'couple to' and 'decouple from' the idler coil and the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil, a parent coil circuit comprising a parent coil and a pivot, where the idler coil is inductively coupled to the parent coil, introducing the NMR probe into a magnetic field, exciting the sample, and rotating the idler coil about the pivot relative to the parent coil to one or both rotate and translate to one or both 'couple to' and 'decouple from' the idler coil and the parent coil, where rotation moves the idler coil into an orthogonal position relative to the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil, a parent coil circuit comprising a parent coil and a pivot, where the idler coil is inductively coupled to the parent coil, introducing the NMR probe into a magnetic field, exciting the sample, and rotating the idler coil about the pivot relative to the parent coil to one or both rotate and translate to one or both 'couple to' and 'decouple from' the idler coil and the parent coil, where rotation moves the idler coil into an orthogonal position relative to the parent coil, where the idler coil is rotated out of an orthogonal position relative to the parent coil to couple the idler coil with the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil and a parent coil circuit comprising a parent coil, where the idler coil is inductively coupled to the parent coil, introducing the NMR probe into a magnetic field, exciting the sample, and moving the idler coil away from the parent coil to decouple the idler coil from the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil and a parent coil circuit comprising a parent coil, where the idler coil is inductively coupled to the parent coil, introducing the NMR probe into a magnetic field, exciting the sample, and moving the parent coil away from the idler coil to decouple the idler coil from the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil and a parent coil circuit comprising a parent coil, where the idler coil is inductively coupled to the parent coil, introducing the NMR probe into a magnetic field, exciting the sample, and orienting the parent coil away from the idler coil to decouple the idler coil from the parent coil.

In an embodiment of the invention, a method to simultaneously obtain a NMR spectrum of two or more nuclei from a sample, comprises the steps of providing a sample, introducing the sample into a high resolution NMR probe including an idler coil circuit comprising an idler coil and a parent coil circuit comprising a parent coil, where the idler coil is inductively coupled to the parent coil, introducing the NMR probe into a magnetic field, exciting the sample, and inserting a metallic screen between the parent coil and the idler coil to decouple the idler coil from the parent coil.

In an embodiment of the invention, a kit for adapting a NMR system to measure dual nuclei comprising an idler coil circuit including an idler coil and a parent coil circuit including a parent coil, where the idler coil is inductively coupled to the parent coil.

In an embodiment of the invention, a kit for adapting a NMR system to measure dual nuclei comprising an idler coil circuit including an idler coil, a parent coil circuit including a parent coil, where the idler coil is inductively coupled to the parent coil, and a pivot, where the idler coil is inductively decoupled from the parent coil by rotating the idler coil relative to the parent coil about the pivot.

In an embodiment of the invention, a kit for adapting a NMR system to measure dual nuclei comprising an idler coil circuit including an idler coil, a parent coil circuit including a parent coil, where the idler coil is inductively coupled to the parent coil, and a metallic screen mounted on a shunt and adapted to be inserted between the parent coil and the idler coil to decouple the idler coil from the parent coil.

In an embodiment of the invention, a kit for adapting a NMR system to measure dual nuclei comprising an idler coil circuit including an idler coil, a parent coil circuit including a parent coil, where the idler coil is inductively coupled to the parent coil, a pivot, where the idler coil is inductively decoupled from the parent coil by rotating the idler coil relative to the parent coil about the pivot, and a metallic screen mounted on a shunt, where the shunt is adapted to be inserted between the parent coil and the idler coil to decouple the idler coil from the parent coil.

While the systems, methods, and devices have been illustrated by the described examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and devices provided herein. Additional advantages and modifications will readily be apparent to those skilled in the art. Therefore, the invention, in its broader aspects, is not limited to the specific details, the representative system, method or device, and illustrative examples shown and described. Accordingly, departures may be made from such details without departing from the spirit or scope of the applicant's general inventive concept. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

TABLE 1

Performance data for capacitive, inductive and normal circuits in a modified OneNMR Probe, where normal refers to an unmodified OneNMR Probe.

| Circuit | Idler × $10^6$ MHz | Obs Nuc | # of Modes | Power$^a$ | PW (90)$^b$ | S/N$^{c,d}$ | S/N (Inductive/ Capacitive)$^e$ |
|---|---|---|---|---|---|---|---|
| 1a) Capacitive | NA | $^1$H | 1 | 25.1 | 10 | 941 | $1.08^{3a/1a}$ |
| 1b) Capacitive | NA | $^{19}$F | 1 | 27.6 | 10.7 | 1144 | $1.07^{3b/1b}$ |
| 2a) Capacitive | NA | $^1$H | 2 | 25.1 | 13.8 | 692 | $1.07^{4a/2a}$ |
| 2b) Capacitive | NA | $^{19}$F | 2 | 27.6 | 16.4 | 729 | $1.16^{4b/2b}$ |
| 3a) Inductive | 582.16 | $^1$H | 1 | 25.1 | 9.3 | 1014 | $1.08^{3a/1a}$ |
| 3b) Inductive | 582.16 | $^{19}$F | 1 | 27.6 | 9.7 | 1221 | $1.07^{4a/2a}$ |
| 4a) Inductive | 582.16 | $^1$H | 2 | 25.1 | 13.2 | 738 | $1.07^{4a/2a}$ |
| 4b) Inductive | 582.16 | $^{19}$F | 2 | 27.6 | 13.7 | 842 | $1.16^{4b/2b}$ |
| 5a) Normal | NA | $^1$H | 1 | 25.1 | 9.5 | 1043 | NA |
| 5b) Normal | NA | $^{19}$F | 1 | 27.6 | 9.8 | 1199 | NA |

Key:
$^a$Watts;
$^b$×10$^{-6}$ seconds;
$^c$0.1% Etrhylbenzene;
$^d$0.05% triflurotoluene;
$^e$Circuit Number;
NA = Not Applicable;

What is claimed is:

1. A method to simultaneously obtain a Nuclear Magnetic Resonance (NMR) spectrum of two or more nuclei from a sample, comprising:
   (a) introducing one or more of a homogeneous or heterogeneous liquid, gas or solid sample into a NMR probe comprising:
      (i) a parent coil circuit including a parent coil within the NMR probe;
      (ii) one or more elements selected from the group consisting of a pivot, a shunt and a screen; and
      (iii) an idler coil circuit including an idler coil;
   (b) introducing the NMR probe into a magnetic field;
   (c) exciting the sample with a Radio Frequency (RF) pulse at a Larmor frequency;
   (d) physically moving the idler coil and/or the screen using the pivot and/or the shunt to inductively couple or decouple the idler coil from the parent coil;
   (e) splitting of a resonance of the parent coil circuit into a first mode and a second mode, where moving the idler coil in step (d) adjusts the coupling constant from zero to a non zero value to split the resonance into the first mode and the second mode; and
   (f) detecting the NMR spectrum including the first mode and the second mode.

2. The method of claim 1, where the first mode is detected simultaneously with second mode.

3. The method of claim 1, further comprising obtaining a NMR spectrum of the sample.

4. The method of claim 1, where the first mode is $^1$H and the second mode is $^{19}$F.

5. The method of claim 1, where the idler coil circuit includes capacitor C1 and inductor L1 and the parent coil circuit includes capacitor C2 and inductor L2, further comprising resonating L1 and L2 at a point approximately halfway between the first mode and the second mode using C1 and C2.

6. The method of claim 5, where C1 and C2 are adjusted to split the resonance into the first mode and the second mode.

7. The method of claim 5, where a coupling constant (k) between the parent coil and the idler coil is given by k=M/√(L1L2), where M is the mutual inductance between L1 and L2.

8. The method of claim 1, where rotation around the pivot moves the idler coil into an orthogonal position relative to the parent coil.

9. The method of claim 1, where the idler coil is rotated out of an orthogonal position relative to the parent coil to couple the idler coil with the parent coil.

10. The method of claim 1, further comprising using the shunt to translate the idler coil away from the parent coil to one or both couple and decouple the idler coil from the parent coil.

11. The method of claim 1, further comprising using the shunt to move the idler coil away from the parent coil to one or both couple and decouple the idler coil from the parent coil.

12. A probe comprising:
 (a) a high resolution Nuclear Magnetic Resonance (NMR) probe containing one or more of a homogeneous or heterogeneous liquid, gas or solid sample;
 (b) a parent coil circuit including a parent coil and an inductor L2;
 (c) one or more elements selected from the group consisting of a pivot, a shunt and a metallic screen; and
 (d) an idler coil circuit including an idler coil and an inductor L1 adapted to allow splitting of a resonance of the parent coil circuit into a first mode and a second mode, where the pivot and/or the shunt are adapted to physically move the idler coil and/or the metallic screen to one or both inductively couple and decouple the idler coil from the parent coil where the coupling constant (k) between the parent coil and idler coil is given by k=M/√(L1L2), where M is the mutual inductance between L1 and L2, where physically moving the idler coil and/or the metallic screen adjusts the coupling constant from zero to a non zero value to split the resonance into the first mode and the second mode.

13. The probe of claim 12, further comprising a pulse generator adapted to apply a RF frequency pulse to the parent coil to one or both couple and decouple the idler coil and the parent coil.

14. The method of claim 1, where the first mode and the second mode are detected simultaneously.

15. A method comprising:
 (a) introducing a sample in an NMR probe into a magnetic field, the NMR probe comprising:
  (i) a parent coil circuit including a parent coil and an inductor L2;
  (ii) one or more elements selected from the group consisting of a pivot, a shunt and a metallic screen; and
  (iii) an idler coil circuit including an idler coil and an inductor L1;
 (b) exciting the sample with a Radio Frequency (RF) pulse at a Larmor frequency to generate a resonance;
 (c) physically moving the idler coil and/or the metallic screen-using the pivot and/or the shunt to inductively couple and/or decouple the idler coil from the parent coil to allow splitting of the resonance of the parent coil, where the coupling constant (k) between the parent coil and idler coil is given by k=M/√(L1L2), where M is the mutual inductance between L1 and L2, where physically moving the idler coil and/or the metallic screen adjusts the coupling constant from zero to a non zero value to split the resonance; and
 (d) inductive coupling splitting the resonance of the parent coil circuit into a first mode and a second mode.

16. The method of claim 15, further comprising undertaking an operation selected from the group consisting of:
 (i) detecting the first mode simultaneously with the second mode;
 (ii) decoupling the first mode simultaneously from the second mode;
 (iii) decoupling the first mode and detecting the second mode; and
 (iv) decoupling the second mode and detecting the first mode.

17. The method of claim 16, further comprising obtaining a NMR spectrum of the sample.

18. The method of claim 16, where the first mode is $^1$H and the second mode is $^{19}$F.

19. The method of claim 18, where the idler coil circuit includes capacitor C1 and the parent coil circuit includes capacitor C2, further comprising resonating L1 and L2 at a point approximately halfway between the first mode and the second mode using C1 and C2.

20. The method of claim 19, where C1 and C2 are adjusted to split the resonance into the first mode and the second mode.

* * * * *